(12) United States Patent
Parris et al.

(10) Patent No.: US 8,776,274 B2
(45) Date of Patent: Jul. 15, 2014

(54) METHODS AND INTEGRATED CIRCUIT PACKAGE FOR SENSING FLUID PROPERTIES

(71) Applicant: Freescale Semiconductor, Inc., Austin, TX (US)

(72) Inventors: Partice M. Parris, Phoenix, AZ (US); Md M. Hoque, Gilbert, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 0 days.

(21) Appl. No.: 13/665,840

(22) Filed: Oct. 31, 2012

(65) Prior Publication Data

US 2014/0117468 A1     May 1, 2014

(51) Int. Cl.
    *H01L 27/14*      (2006.01)
    *H01L 29/82*      (2006.01)
    *H01L 29/84*      (2006.01)

(52) U.S. Cl.
    USPC .................. 2/414; 257/298; 438/301; 365/18

(58) Field of Classification Search
    USPC ...................... 257/298, E27.084; 365/185.18; 438/301
    See application file for complete search history.

(56) References Cited

U.S. PATENT DOCUMENTS

| | | | |
|---|---|---|---|
| 2004/0113801 A1* | 6/2004 | Gustafson et al. | 340/604 |
| 2004/0130328 A1* | 7/2004 | Koo et al. | 324/536 |
| 2006/0202692 A1* | 9/2006 | Tatschl et al. | 324/252 |
| 2008/0238446 A1* | 10/2008 | DeNatale et al. | 324/663 |
| 2009/0007705 A1* | 1/2009 | McLean et al. | 73/865 |
| 2011/0241706 A1* | 10/2011 | Norton et al. | 324/686 |
| 2011/0299337 A1 | 12/2011 | Parris et al. | |

FOREIGN PATENT DOCUMENTS

WO     2008081393 A     7/2008

OTHER PUBLICATIONS

K. G. Ong, K. Zeng and C. A. Grimes, A wireless. passive carbon nanotube-based gas sensor, IEEE Sensors J., Apr. 2002, pp. 82-88, vol. 2, No. 2, PSU, Merrimack College, Univ. of Kentucky, MTU.
B. E. Horton, S. Schweitzer, A. J. Derouin and K. G. Ong, A Varactor-Based, Inductively Coupled Wireless pH Sensor, IEEE Sensors J., Apr. 2011, pp. 1061-1066, vol. 11, No. 4., Mich. Tech. Un.
E. L. Tan, W. N. Ng, R. Shao, B. D. Pereles and K. G. Ong, A Wireless, Passive Sensor for Quantifying Packaged Food Quality, Sensors, Sep. 2007, pp. 1747-1756, vol. 7, PSU, Merrimack College, Univ. of Kentucky, MTU.

(Continued)

Primary Examiner — Phuc Dang
(74) Attorney, Agent, or Firm — The Mason Group Patent Specialists LLC; Valerie M. Davis

(57) ABSTRACT

An integrated circuit package for sensing fluid properties includes: a substrate made of semiconductor material; a fluid property measurement circuit formed on the substrate; and a sensor circuit coupled to the fluid property measurement circuit within a same integrated circuit package. The sensor circuit is configured to generate a field that interacts with the fluid. The fluid property measurement circuit is configured to determine a change in a property of the sensor circuit as results from the field interacting with the fluid and is further configured to determine a property of the fluid based on the change in the property of the sensor circuit.

20 Claims, 17 Drawing Sheets

(56) References Cited

OTHER PUBLICATIONS

G. Laurent et al., DNA Electrical Detection Based on Inductor Resonance Frequency in Standard CMOS Technology, Proc. 2003 ESSCIRC, 2003, pp. 337-340, Univ. Cath. de Louvain and Notre Dame de la Paix, Belgium.

G. Stojanovic, M. Radovanovic, M. Malesev and V. Radonjanin, Monitoring of Water Content in Building Materials Using a Wireless passive Sensor, Sensors, Apr. 2010, pp. 4270-4280, vol. 10, Univ. Novi Sad, Serbia.

K. G. Ong, J. S. Bitier, C. A. Grimes, L. G. Puckett and L. G. Bachas, Remote Query Resonant-Circuit Sensors for Monitoring of Bacteria Growth: Application to Food Quality Control, Sensors, Jun. 2002, pp. 219-232, vol. 2, PSU, Merrimack College, Univ. of Kentucky, MTU.

M. Lei, A. Baldi, E. Nuxoll, R. Siegel and B. Ziaie, Hydrogel-based microsensors for wireless chemical monitoring, Biomed. Microdevices., 2009, pp. 529-538, vol. 11, U. Minn., Purdue.

Michael E. Van Steenberg et al., Inductive and Capacitive Sensor Arrays for In Situ Composition Arrays, Proc. 2001 IEEE Aerospace Conference, 2001, pp. 299-309, vol. 1, NASA.

* cited by examiner

METHODS AND INTEGRATED CIRCUIT PACKAGE FOR SENSING FLUID PROPERTIES

FIELD

The present disclosure relates generally to fluid sensors and more particularly to methods and an integrated circuit package used to sense fluid properties or characteristics.

BACKGROUND

Integrated circuits (ICs) are currently used to sense some properties of a fluid. For example, Ion-Sensitive Field Effect Transistors (ISFETs) fabricated using complementary metal-oxide semiconductor (CMOS) processing technology are used to sense an ion concentration of an electrolytic solution (i.e., ion concentrated fluid). More particularly, the ISFET is a MOSFET formed on a substrate, such as silicon, and comprises a source and drain region with a channel therebetween. The ISFET further comprises a floating gate region that is electrically connected to ion concentrated fluid via a metal sense plate and one or more other metal interconnects or structures. During operation of the ISFET, in general, the ion concentration within the fluid results in a corresponding electrical bias of the floating gate. This bias results in a measurable change in channel conductivity within the channel between the source and drain. In this manner, it can be said that the ISFET directly senses the ion concentration of the fluid through its source/drain channel conductivity.

Such an ISFET structure has some shortcomings, however. For example, the threshold voltage (Vt) at neutral pH of such devices is known to vary widely. These deleterious effects are primarily attributed to the presence of fixed charge within the floating gate dielectric (and/or a passivation layer) as well as process-induced charges within the floating gate of the ISFET. Consequently, the electrical behavior of the ISFET (with respect to a given ion concentration of the fluid) can be difficult to predict, unless sufficient care is exercised in the manufacturing phase.

Methods such as ultraviolet erase processes and voltage trimming techniques have been used to address the varying threshold voltages of ISFETs. However, in order to sense the ion concentration of the fluid, it is required that at least a portion of the IC be directly exposed to the fluid. Unless additional material cost is factored into the IC fabrication process to protect the exposed IC components, the IC can suffer corrosive effects from the fluid exposure, thereby limiting its lifetime.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
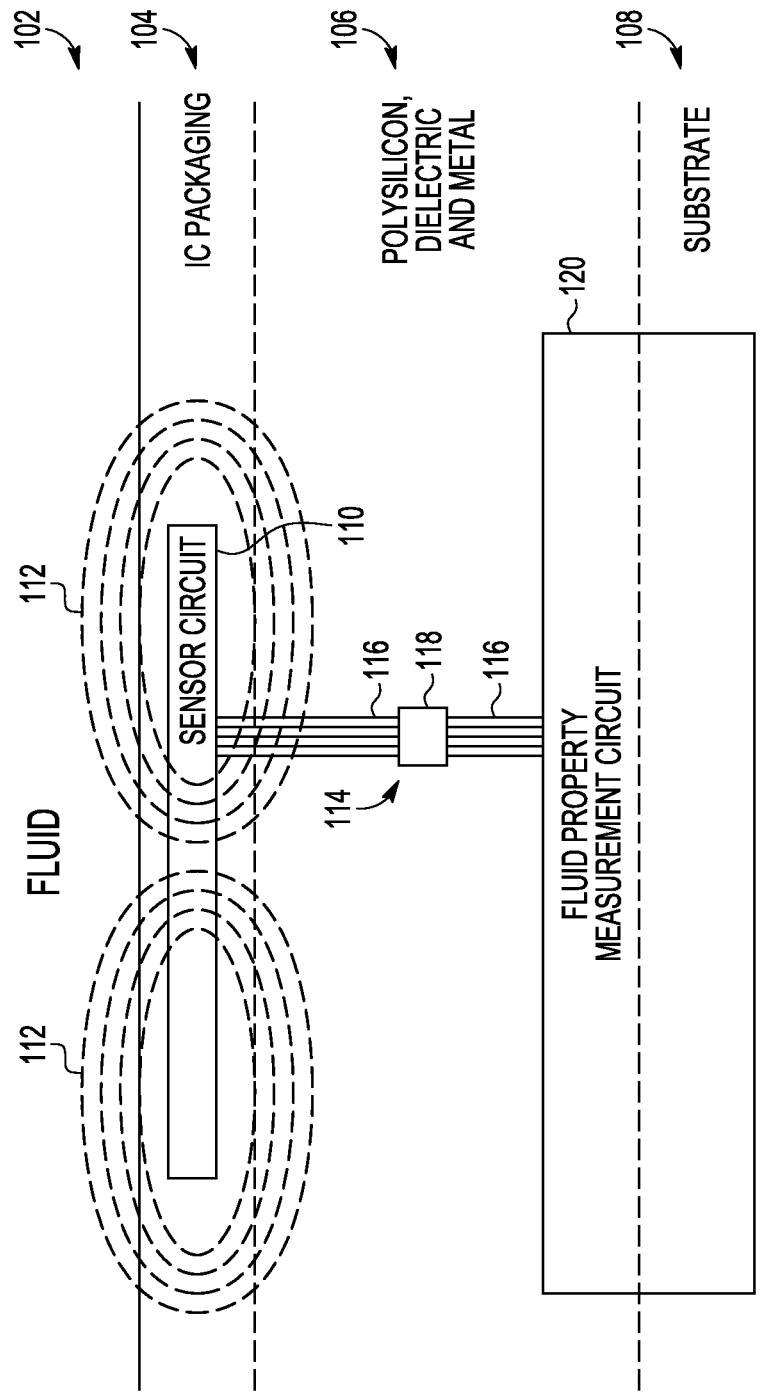
FIG. 1 is a conceptual cross-sectional view of an integrated circuit package for sensing one or more properties of a fluid, in accordance with an embodiment.

The present invention is illustrated by way of example and is not limited by the accompanying figures, in which like references indicate similar elements. Skilled artisans will appreciate that elements in the figures are illustrated for simplicity and clarity and have not necessarily been drawn to scale. For example, the dimensions of some of the elements in the figures may be exaggerated relative to other elements to help improve the understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

In accordance with an embodiment of the present disclosure is an integrated circuit package for sensing fluid properties. The integrated circuit package includes: a substrate made of semiconductor material; a fluid property measurement circuit formed on the substrate; and a sensor circuit coupled to the fluid property measurement circuit within a same integrated circuit package. The sensor circuit is configured to generate a field that interacts with the fluid. The fluid property measurement circuit is configured to determine a change in a property of the sensor circuit as results from the field interacting with the fluid and is further configured to determine a property of the fluid based on the change in the property of the sensor circuit.

In accordance with another embodiment of the present disclosure is a method of fabricating an integrated circuit package for sensing fluid properties. The method includes: forming a fluid property measurement circuit on a substrate; and forming a sensor circuit that is configured to generate a field that interacts with a fluid, wherein the sensor circuit and the fluid property measurement circuit are electrically coupled together and formed within a same integrated circuit package. The fabricated fluid property measurement circuit is configured to determine a change in a property of the sensor circuit as results from the field interacting with the fluid and is further configured to determine a property of the fluid based on the change in the property of the sensor circuit.

In accordance with yet another embodiment of the present disclosure is a method performed by an integrated circuit package for determining fluid properties. The method includes: sensing a property of a fluid using a first field that is generated by a sensor circuit and that interacts with the fluid; and determining, by a fluid property measurement circuit formed on a substrate and coupled to the sensor circuit within a same integrated circuit package, a change in the property of the sensor circuit associated with the first field interacting with the fluid. The method further includes determining, by the fluid property measurement circuit, the sensed property of the fluid using the determined change in the property of the sensor circuit.

Turning now to FIG. 1, shown therein is a conceptual cross-sectional view of an integrated circuit package 100 for sensing one or more properties of a fluid 102, in accordance with an embodiment. The fluid 102 is a solution containing free ions (also referred to herein interchangeably an electrolytic solution or ionic solution), which makes the solution electrically conductive. IC package 100 includes a fluid property measurement circuit 120 and a sensor circuit 110 that are coupled (in this particular embodiment electrically connected via metal interconnects 114) within the same IC package 100. As used herein, an IC package is defined as one or more IC chips and/or other components coupled to and/or included within the same IC packaging 104 as a single integrated physical unit.

As illustrated in FIG. 1, the interconnected sensor circuit 110 and fluid property measurement circuit 120 are included or formed on the same IC chip. This may enable one or more of a smaller IC package, lower cost, or better reliability than embodiments where the interconnected sensor circuit 110 and fluid property measurement circuit 120 are included or formed on different IC chips. An IC chip is defined as an electronic circuit comprising interconnected (i.e., coupled) electronic components (active, passive, or a combination) formed on a same piece of substrate using an IC fabrication process. Packaging is defined as the material used to hold, contain, support, mount, enclose, encapsulate, or seal the sensor circuit 110 and the fluid property measurement circuit 120 as a single unit.

IC chip 100 is manufactured using any suitable semiconductor device fabrication process (also referred to herein as an IC fabrication process), including known IC fabrication processes such as ones implementing CMOS technology. As used herein, the term IC fabrication process also includes the step of packaging. The IC fabrication process begins with a substrate comprising semiconductor material such as Silicon, Germanium, or other semiconductor material and includes multiple process steps used to create interconnected electronic components on the substrate. These process steps include, for example, doping or ion implantation, etching, deposition of various layers of materials, and photolithographic patterning. The process steps result in interconnected electronic components being formed in multiple layers of material (e.g., 106) on a substrate, wherein the multiple layers include for example, polysilicon, metal, dielectric (such as $SiO_2$), and passivation. As used herein, all of the electronic components formed on a single IC chip that is fabricated starting with a given piece of substrate are referred to, in general, as being "formed on" that piece of substrate.

The fluid property measurement circuit 120 comprises a set of electronic components formed on a substrate 108. The particular set of electronic components is determined by the type or types of sensor circuit 110 properties that the fluid property measurement circuit is designed to detect or measure. Such circuits 120 include, but are not limited to, receivers, low noise amplifiers, frequency (e.g., radio frequency (RF)) sensing circuits, digital signal processors (DSPs), microcontroller units (MCUs), etc. Accordingly, depending on the sensor circuit 110 implementation, the fluid property measurement circuit contains one or more active and/or passive components such as transistors (e.g., metal-oxide field effect transistors (MOSFETs)), resistors, capacitors, etc. As such, some portions of the fluid property measurement circuit 120 are formed directly in the substrate 108 (including drain and source regions of a MOSFET for instance) through doping and ion implantation. Other portions of the fluid property measurement circuit 120 (such as gate regions of a MOSFET or plates and dielectric of a capacitor, as examples) are formed in other material layers 106 deposited on the substrate 108. These other material layers 106 comprise one or more layers of polysilicon, dielectric, and/or metal layers in various types, amounts and combinations depending on the particular electronic components and interconnects formed therein.

The sensor circuit 110 comprises at least one (i.e., one or more) electronic components that operate to create a field 112 (e.g., a self-induced electromagnetic field, a fringe field, a mutually-induced electromagnetic field, a parallel plate field, etc.) that interacts with the fluid 102 such as by contacting, penetrating or extending a given depth into the fluid. The field "interacting with" the fluid means that the fluid affects a change to the field, which in turn affects one or more intrinsic properties of the sensor circuit. In one embodiment, the sensor circuit comprises at least one inductor (L) component. For example, the at least one inductor component comprises a first inductor component having a first geometry and a second inductor component having a second geometry that is different than the first geometry of the first inductor component. In a further embodiment, the sensor circuit comprises at least one capacitor (C) component such as an interdigitated comb capacitor (also referred to as a co-planar capacitor). For example, the at least one capacitor component comprises a first capacitor component having a first geometry and a second capacitor component having a second geometry that is different than the first geometry of the first capacitor component. Moreover, other types of capacitor types can be used including, but not limited to, metal-insulator-metal (MIM) capacitors, non-co-planar capacitors, and non-finger co-planar capacitors (e.g., fractal or dots). In yet another embodiment, the sensor circuit comprises at least one inductor component and at least one capacitor component to form one or more LC or RLC circuits.

As stated above, and in accordance with the present teachings, the sensor circuit 110 and the fluid property measurement circuit 120 are coupled within the same IC package 100. This IC package 100 includes packaging material 104 configured or designed to hold, contain, support, mount, enclose, encapsulate, or seal the sensor circuit 110 and the fluid property measurement circuit 120 as a single unit. In an embodiment, the IC package 100 comprises packaging material 104 configured to prevent direct physical contact of the fluid 102 with the substrate 108, the fluid property measurement circuit 120, and the sensor circuit 110. In this embodiment, the IC package 100 is designed to be impenetrable or impervious to the fluid 102, which means that only the field 112 of the sensor circuit 110 interacts with the fluid. This is in contrast with prior art sensors, including known ISFET sensor technology, which require the fluid to physically contact at least a portion of the sensor arrangement in order to sense the fluid properties.

In one embodiment, the sensor circuit 110 and the fluid property measurement circuit 120 are sealed in plastic packaging material 104 or encased in ceramic packaging material 104 that is impervious to the fluid 102. However, in alternative embodiments, the packaging material 104 allows the fluid 102 to contact the circuit components within the IC package 100, to at least some extent; and/or a different type of IC packaging 104 is used, including, but not limited to, a printed circuit board having mounted thereon the sensor circuit 110 and the fluid property measurement circuit 120. The IC packaging 104 can also comprise a packaging substrate or lead frame to which the die having the sensor circuit 110 and the fluid property measurement circuit 120 is mounted.

The sensor circuit 110 and the fluid property measurement circuit 120 are communicatively coupled to enable the fluid property measurement circuit 120 to determine a change in a property of the sensor circuit 110 as results from its field interacting with the fluid. In the embodiment shown, the coupling comprises a direct electrical connection through a set of one or more electrical connectors 114 formed in one or more metal layers (e.g., 118) of the IC chip, wherein the metal layer(s) 118 are interconnected through wires, interconnects, or vias (vertical interconnect accesses) 116. As shown, the interconnects (e.g., 116) in FIGS. 1-3 and 5-15 are direct vertical connections between circuit components through a single metal layer. However, in alternate arrangements, at least some of the interconnects pass through multiple metal layers and/or "zig zag" through the layers 106 between the circuit components. Moreover, depending on the configuration (i.e., the particular components and arrangements of those components) of a given fluid property measurement circuit, the sensor circuit (e.g., an inductor or capacitor of the sensor circuit) could couple to a gate, drain, or source of a transistor component of the fluid property measurement circuit.

Figure 2:
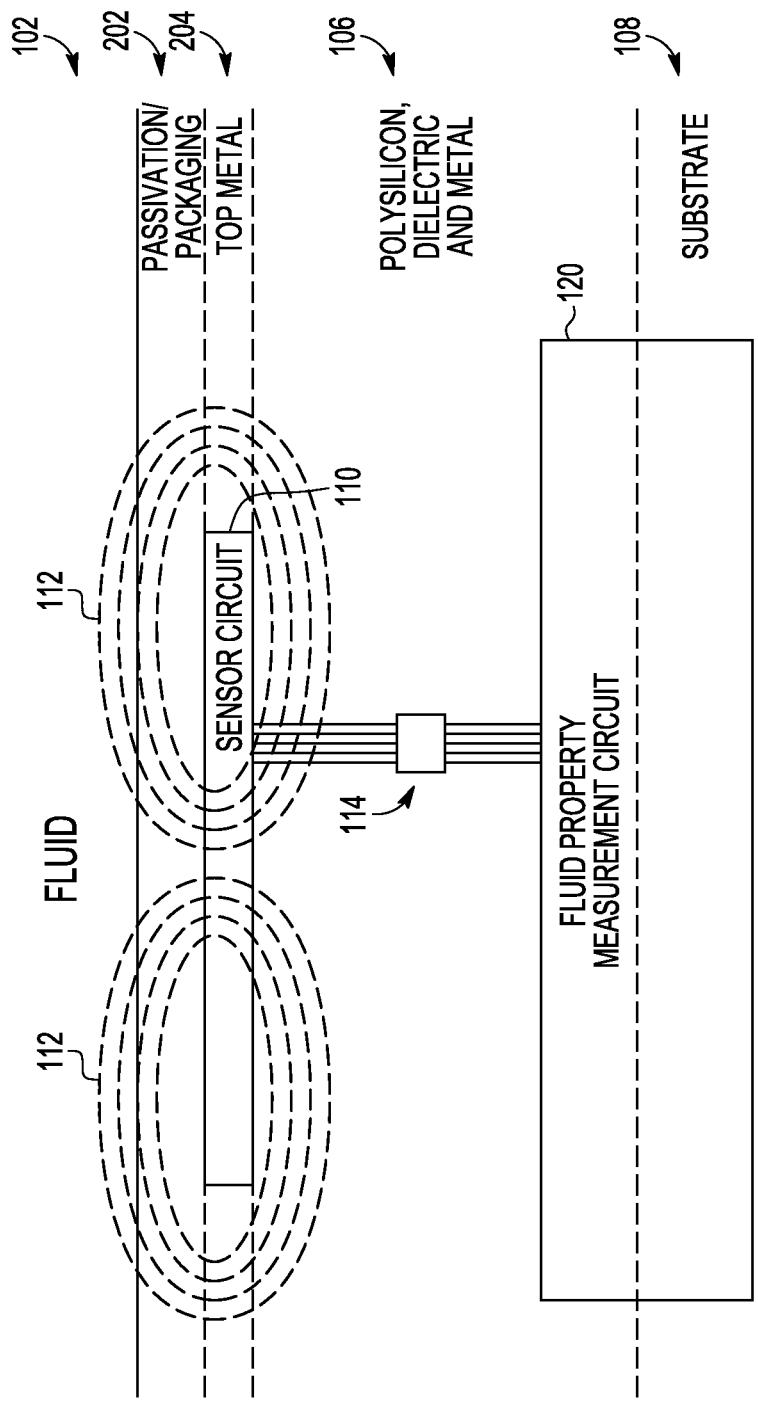
FIG. 2 is a conceptual cross-sectional view of an integrated circuit package for sensing one or more properties of a fluid, in accordance with another embodiment.

Also, as stated earlier, in accordance with the present teachings, the sensor circuit 110 and the fluid property measurement circuit 120 are included within a same IC packaging 104. The sensor circuit 110 can be located within the IC packaging 104 at different positions relative to the fluid property measurement circuit 120, as shown in general with respect to FIGS. 2 and 3. For example, as shown in FIG. 2, in one embodiment, the sensor circuit 110 is formed in at least a top metal layer 204 of the integrated circuit chip 100, and the integrated circuit chip further comprises a passivation layer 202 covering the top metal layer 204. In the embodiments shown with respect to FIGS. 1-3 and 5-15, the passivation layer comprises any combination of (i.e., at least one of) silicon oxide, silicon nitride, or silicon oxi-nitride having a "standard" thickness on the order of um or hundreds of nm as opposed to being a "thin" layer on the order of tens of nm or less. The passivation layer 202 acts as a shielding outer layer for the top metal layer 204 and comprises a coating of material to create a shell against corrosion. In this embodiment, the coupling between the sensor circuit 110 and the fluid property measurement circuit comprises a direct electrical connection through the set of one or more electrical connectors 114.

Figure 3:
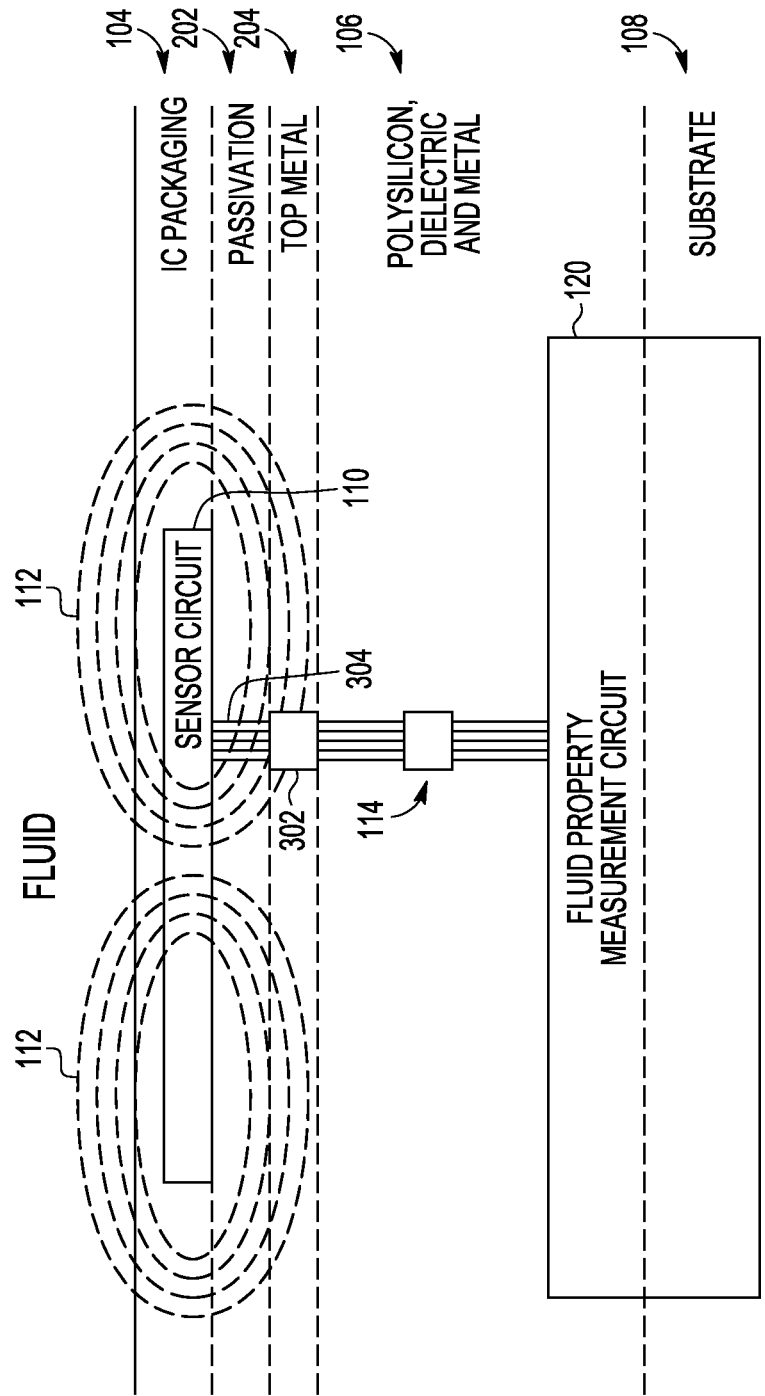
FIG. 3 is a conceptual cross-sectional view of an integrated circuit package for sensing one or more properties of a fluid, in accordance with another embodiment.

In an alternative embodiment, as illustrated with respect to FIG. 3, the IC package 100 further comprises the passivation layer 202 and the metal layer 204 formed between the sensor circuit 110 and the fluid property measurement circuit 120, wherein the sensor circuit 110 is formed on top of the passivation layer 202. In accordance with one example implementation of this embodiment, the sensor circuit 110 (comprising one or more inductors, capacitors, LC circuits, etc.) is physically interconnected to the fluid property measurement circuit 120 via metal pads 302 formed in the top metal layer 204 and one or more metal electrical connectors 114 formed in material layers 106. In such a case, metal (e.g., gold) from which the sensor circuit 110 is fabricated extends into an opening 304 in the passivation layer 202 to complete the electrical connection between the sensor circuit 110 and the fluid property measurement circuit 120. Forming the sensor circuit on top of the passivation layer enables the use of material that can withstand higher power to, thereby, increase the range or distance of the field generated by the sensor circuit. This enables the IC package to be placed further from the fluid but still have the field of the sensor circuit interact with the fluid.

Alternative arrangements of the sensor circuit 110 and the fluid property measurement circuit 120 and the coupling between these circuits are possible. For example, in one alternative embodiment, instead of being included on a single IC chip, the sensor circuit and the fluid property measurement circuit are each included on separate IC chips, but still contained within the same IC packaging. This packaging could include: plastic or ceramic packaging enclosing the chips, which may or may not be impervious to the fluid; a printed circuit board having mounted thereon the separate chips; etc. In another alternative embodiment, the sensor circuit and the fluid property measurement circuit are wirelessly coupled within the same IC packaging. In such a case, the sensor circuit communicates the data or information (relating to the change in the property of the sensor circuit as results from the field contacting the fluid) to the fluid property measurement circuit using a wireless signal, such as a radio frequency (RF) signal. Any conventional RF transmission circuits and techniques can be used for this purpose. Any of the IC packages shown in FIGS. 1-3 and 5-15 can be modified using one or both of these alternative arrangements.

Figure 4:
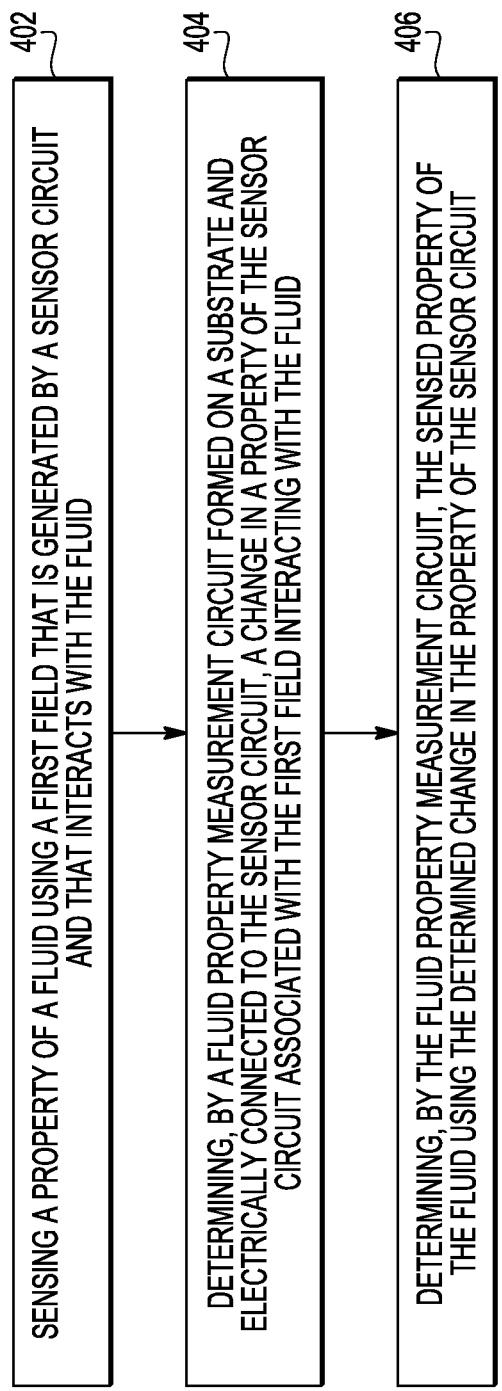
FIG. 4 is a flow diagram illustrating a method performed by an integrated circuit package for determining one or more properties of a fluid, in accordance with an embodiment.

Turning now to FIG. 4, therein is shown a flow diagram illustrating a general method 400 performed by an integrated circuit package for determining one or more properties of a fluid, in accordance with an embodiment. Method 400 can be performed by any one of the IC packages shown in FIGS. 1-3 and 5-15, for example. Sensing a property of a fluid using a field that is generated by a sensor circuit and that interacts with the fluid, is performed at 402. More particularly, a field (e.g., 112) generated by the sensor circuit (e.g., 110) interacts with the fluid (e.g., 102) during operation of the IC package (e.g., 100). When the field interacts with the fluid, the fluid affects a change to the field, which in turn affects an intrinsic property or properties of the sensor circuit.

More particularly, the electrically conductive free ions within the fluid change the field (e.g., an electrical, magnetic, or electromagnetic field) created by the sensor circuit, which changes one or more intrinsic properties of the sensor circuit such as a self-inductance of an inductor within the sensor circuit, a capacitance of a capacitor within the sensor circuit, and/or a resonant frequency of an LC circuit within the sensor circuit. Accordingly, it can be said that the field of the sensor circuit is sensing a property of the fluid instead of the sensor circuit itself (i.e., through a direct physical contact with the fluid) sensing the property of the fluid as in the prior art such as ISFETs.

Take, for example, a simple sensor circuit comprising one inductor. During operation, a current through the inductor (e.g., using an on-chip or off-chip current source) creates a magnetic field around the inductor. The magnetic field affects movement of the ions within the fluid. This movement of ions within the fluid operates to change the magnetic field within and close to the fluid and, therefore, to change the magnetic field generated by the inductor. This field determines the inductance, L, (also referred to herein as the self-inductance) of the inductor. Since the field is changed by its contact with the fluid, the fluid is able to impact the inductance and quality factor, Q, of the inductor through its interaction with the field. Ion-bearing fluids can change the magnetic field through the impact of their permeability and through the magnetic field screening action of the ions within them. Non-ionic fluids change the field through their permeability. The change in magnetic field alters L, and Q of the inductor, as well as its resonant frequency. The result is a shift in the L versus frequency and Q versus frequency curves. Any circuit technique used to detect these changes will, thus, be detecting properties of the fluid.

The depth of penetration of the magnetic field into the fluid depends at least in part upon the geometry of the inductor-fluid arrangement, as well as the fluid permeability and ionic content. The geometry of the inductor is defined by one or more of the following parameters: the number of turns of the inductor; the spacing in between the turns; one or more characteristic diameters of the inductor; or the distance of the sensor circuit from the fluid with range of field generally increasing with inductor size. Furthermore, the penetration depth of the magnetic field is limited by the ion concentration in the fluid. More particularly, where the number of mobile ions in the fluid increases, the more difficult it becomes for the field to penetrate the fluid at any given frequency. In addition, the response of the ions within the fluid is frequency dependent due, in part, to the decreased response of heavier ions or ions in more viscous fluids to higher frequency fields.

To illustrate this above-described interdependence between magnetic field, sensor circuit geometry, fluid composition, and self-inductance for a sensor circuit comprising a single inductor, the following equation is provided for determining the inductance (i.e., the self-inductance) of the inductor.

$$\text{Inductance} = L = K_1 * \mu_{\text{eff}} * \frac{n^2 d_{\text{average}}}{1 + K_2 \rho}, \text{ where}$$

$K_1$ and $K_2$ are layout—dependent coefficients
$\mu_{\text{eff}}$ is an effective permeability, dependent on the geometric fluid—inductor arrangement and permeabilities of the materials through which the field passes
n is the number of turns in the inductor.

$d_{\text{average}}$ is the arithmetic mean of the inner and outer diameters of the inductor $$d_{\text{average}} = 0.5 * (d_{\text{inner}} + d_{\text{outer}})$$

$\rho$ is the "fill ratio"

$$\rho = \frac{d_{\text{outer}} - d_{\text{inner}}}{d_{\text{outer}} + d_{\text{inner}}}$$

Similarly, equations could be derived to model or approximate features associated with different configurations of sensor circuits.

For a sensor circuit comprising a single interdigitated comb capacitor (also sometimes referred to as a comb capacitor, an in-plane capacitor, an interdigitated capacitor, a coplanar capacitor or a fringe capacitor), the field generated by this component (when it is charged) is called a "fringe" or "fringing" electric field. More particularly, the fringe capacitor comprises a set of parallel plates each having a plurality of "fingers" extending from the plate with gaps in between the fingers. The respective fingers of the plates are arranged within a same plane such that each two consecutive fingers within the plane are from a different one of the plates.

An arrangement of the parallel plates in this manner creates a fringing field in a region below, above and extending outward from the fingers, e.g., originating and emanating from the finger tips and/or other finger surfaces. Characteristics of the fringing field (e.g., extent and/or magnitude of the electric field) are determined by the characteristics (e.g. permittivity) of the media through which the field passes and the geometry of the fringe capacitor. The geometry of a fringe capacitor is defined by one or more of the following parameters: the size of the gap between the fingers of each plate, the numbers of fingers on each plate, finger geometry of each plate (e.g., finger width, finger length and finger height), etc. Upon placement of the sensor circuit close enough to the fluid to enable the fringing field to contact the fluid, the fluid changes the fringing field. This, in turn, affects properties of the fringe capacitor, particularly its capacitance. Non-ionic fluids can influence the field since their permittivity is different from that of the medium previously occupying the volume close to the fringe capacitor. Ionic fluids also change the field by limiting its penetration into the bulk of the fluid. The distance scale over which the electric field decays in the fluid is inversely proportional to the square root of its ionic concentration.

In another example sensor circuit implementation comprising at least one LC circuit, an AC power source is provided to an LC circuit such that it creates an electromagnetic field that is associated with an oscillation or resonant frequency. The resonant frequency is dependent on the geometries (and corresponding inductance and capacitance values) of the constituent inductor and capacitor components. When the electromagnetic field interacts with the fluid, the ions in the fluid change the inductance and/or capacitance values of the LC circuit. This changes the LC product and, hence, the resonant frequency of the LC circuit.

Turning back to method 400, the fluid property measurement circuit determines (at 404) a change in a property of the sensor circuit associated with the field (generated by the sensor circuit) contacting the fluid. For example, this involves, prior to allowing the field of the sensor circuit to contact the fluid, determining known values (e.g., a known resonant frequency, inductance value, capacitance value, etc.) for the properties of the sensor circuit that will be tracked by the fluid property measurement circuit, which is referred to herein as a known calibration state.

In one embodiment, the sensor circuit properties are measured and the values stored within the IC package containing the sensor circuit and the fluid property measurement circuit. In an embodiment, the measured values are stored within a memory device (e.g., flash memory) associated with a microprocessor on the chip that includes the fluid property measurement circuit. Accordingly, the fluid property measurement circuit determines or measures the particular property for the sensor circuit when its field interacts with the fluid, and compares this measured value to the corresponding stored values to determine the change in the property for the sensor circuit as a result of its field contacting the fluid. In a related embodiment, the sensor circuit properties are trimmed to a desired value before the field is allowed to interact with the fluid. The fluid property measurement circuit then measures the difference between the initial trimmed property value and the value of the property after the start of the interaction between the fluid and the sensor circuit. An example of this would be adjusting the value of the resistance R, in a sensor circuit, which is comprised of an RLC resonator.

In another embodiment, the IC package containing the sensor circuit and the fluid property measurement circuit also includes a reference circuit formed on the substrate and coupled to the fluid property measurement circuit, wherein the reference circuit is configured to generate a field that matches the field generated by the sensor circuit in a known calibration state. However, the field of the reference circuit is not allowed to contact the fluid. Accordingly, the fluid property measurement circuit determines or measures the particular property for the sensor circuit when its field interacts with the fluid, and compares this measured value to the corresponding value for the same property of the reference circuit, to determine the change in the property for the sensor circuit as a result of its field contacting the fluid. This embodiment allows the fluid property measurement circuit to generate more accurate determinations over time and temperature variations, for instance, of the sensor circuit.

As indicated above, any of a number of properties of the sensor circuit can be tracked by the fluid property measurement circuit. However, the tracking of some properties, for instance inductance or capacitance values would require the fluid property measurement circuit to include more complicated circuitry. As an example of simplifying the circuitry of the fluid property measurement circuit, the property that this circuit can be configured to measure is a frequency change associated with the sensor circuit such as a change in resonant frequency or a change in frequency of the field generated by the sensor circuit. Such a fluid property measurement circuit is referred to as a frequency sensing or frequency sensitive circuit. Using a frequency sensitive circuit as the fluid property measurement circuit has the benefit of enabling the calibration of the sensor and reference circuit (if used) to a certain frequency for a particular type of fluid, since the response of the ions in the fluid is frequency dependent.

Accordingly, in an embodiment (where the sensor circuit comprises an LC circuit), determining the change in the property of the sensor circuit comprises determining a change in resonant frequency of the sensor circuit. In one particular embodiment, determining the change in resonant frequency of the sensor circuit comprises comparing a first resonant frequency measured for the sensor circuit while its field interacts with the fluid to a second resonant frequency of a reference circuit within the same integrated circuit package and positioned to prevent a field generated by the reference circuit from contacting the fluid. This particular embodiment uses a reference LC circuit having "matched" components (i.e., the same or substantially the same) to the sensor circuit and thereby having the same or substantially the same resonant frequency as that of the sensor circuit when the sensor circuit is not interacting with the fluid. When the field of the sensor circuit interacts with the fluid, the fluid property measurement circuit compares the resonant frequency of the sensor circuit to the resonant frequency of the reference circuit to determine the change in the property of the sensor circuit, in this case the change in the resonant frequency.

In another embodiment, the fluid property measurement circuit is configured similar to a phase-locked loop (PLL) configuration. More particularly, the PLL is configured to move its output frequency to match the frequency of the LC sensor circuit moving from a nominal (i.e., calibrated) value to the value generated after the field generated by the sensor circuit interacts with the fluid. The PLL-based circuit can be further configured to provide a measure of the change in the resonant frequency.

At 406 of method 400, the fluid property measurement circuit determines the sensed property of the fluid using the determined change in the property of the sensor circuit. In an embodiment, a database is built off-line that stores the characteristics or properties (e.g., ion concentration, frequency response, etc.) for different fluids and fluid concentrations at different frequencies for a given sensor circuit configuration. The fluid properties and characteristics data from this database are stored within a memory device associated with or included within the IC package. During operation of the IC package, the fluid property measurement circuit is used to compare a measured response to the stored data for one or more fluids to determine a property of the fluid such as the type of fluid or a concentration of a particular ion within the fluid. The complexity of the comparisons is limited, in part, by the storage capacity of the memory device, the contents of the database and the processing power available. The local database could also be supplemented with a remote database.

Figure 17:
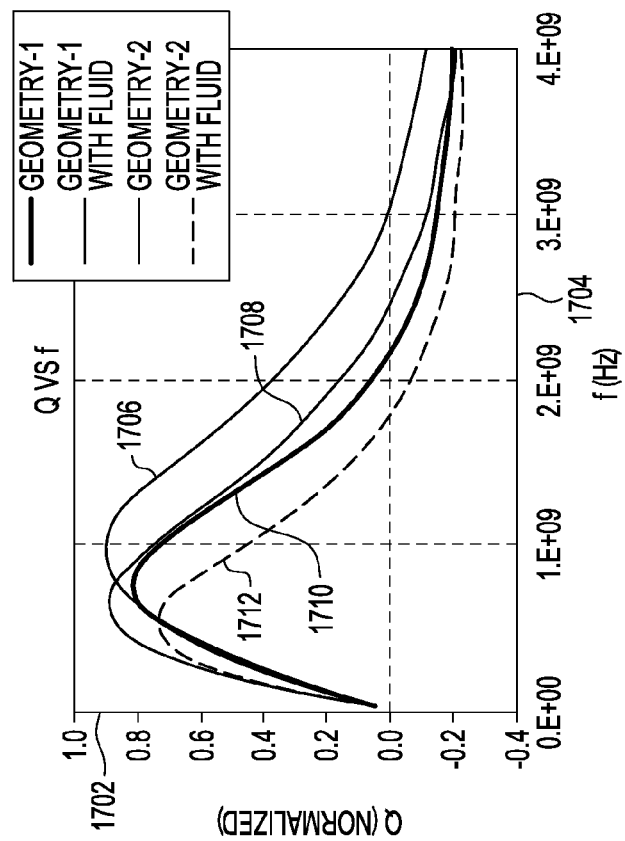
FIG. 17 is a graphical representation illustrating embodiments of the present disclosure.
Figure 16:
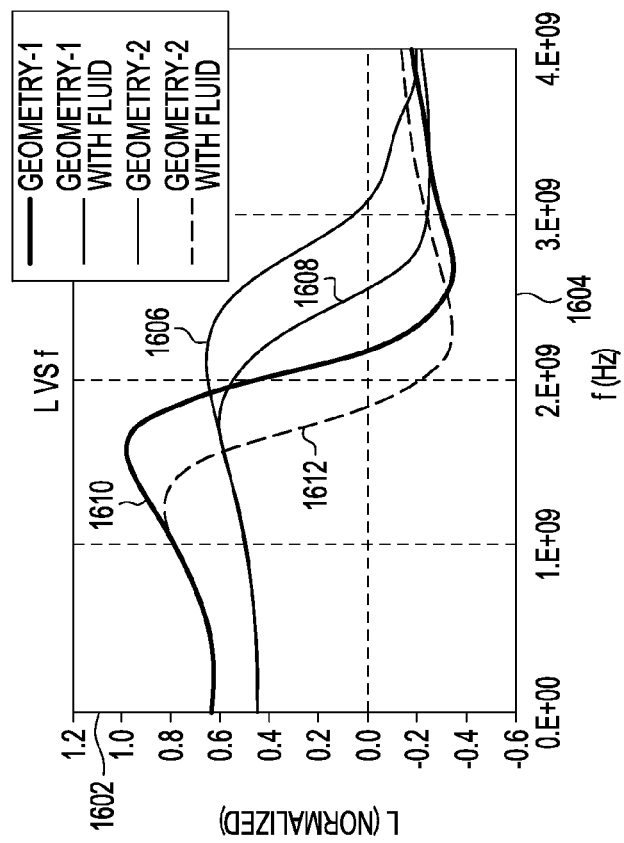
FIG. 16 is a graphical representation illustrating embodiments of the present disclosure.

FIGS. 16 and 17 show some illustrative frequency responses associated with example sensor circuit configurations. More particularly, FIG. 16 illustrates a graphical representation 1600 showing plots 1606-1612 of normalized inductance (axis 1602) versus frequency in Hz (axis 1604) for a sensor circuit comprising an inductor of a particular design. Plots 1606 and 1610 show the inductance as a function of frequency for a first and second inductor, respectively, having different geometries, when the field of the circuit is not interacting with the fluid. The fluid-induced shift in inductance as a function of frequency for the first and second inductor designs is illustrated in plots 1608 and 1612, respectively. Evident is the shift in resonant frequency for both geometries.

FIG. 17 illustrates a graphical representation 1700 showing plots 1706-1712 of Q (axis 1702) versus frequency in Hz (axis 1704) for sensor circuit comprising an inductors of the same design as in FIG. 16. Plots 1706 and 1710 show the Q as a function of frequency for the first and second inductor designs, respectively, when the field of the circuit is not interacting with the fluid. The fluid-induced shift in Q as a function of frequency for the first and second inductor designs is illustrated in plots 1708 and 1712, respectively. The fluid induced shift in the frequency dependence of Q is evident, as is the shift in resonant frequency.

Plots such as those shown in FIGS. 16 and 17 are examples of characteristics that can be used to build the database mentioned above. The data from this database can be stored in the IC package to use in determining properties or characteristics of a fluid being sensed and/or identify the fluid or types of ions within the fluid being sensed.

In another embodiment, the fluid is manipulated and changes to the property of the sensor circuit are measured to determine a property of the fluid. One example is the use of temperature change or the addition of reactants to change the composition of the fluid, especially its ionic composition. Continuous measurement of the behavior of the fluid and its ions allows progress of the reaction to be monitored. Using the appropriate database, additional inferences about fluid properties can be made. If a stimulus is introduced into the fluid a known distance from the sensor circuit and the time delay between the introduction of the stimulus and the observation of a change in fluid properties is measured, the relevant flow rate of the fluid and species within it can be measured. In one example implementation, the fluid is heated to determine a flow rate of the ions within the fluid, which can then be used, for instance, to identify the type of ions and perhaps the concentration of ions within the fluid. For the flow rate example, a heater is positioned near or within the fluid at a known distance from the sensor circuit. Upon using the heater to increase the temperature of the fluid, the fluid properties close to the heater can be changed. An internal clock can measure the delay between the onset of heating and the time that the field of the sensor circuit senses a change in the fluid due to the temperature change. Since distance and time are now known, flow rate can be determined.

FIGS. 5-15 illustrate various embodiments of the sensor circuit 110 within an IC package, in accordance with the present teachings. These embodiments are not meant to be exhaustive, but only to provide some example configurations for the sensor circuit. The particular configuration used for a given application depends, at least in part, on the type of fluid being sensed. Moreover, some of the reference numbers from FIGS. 1-3 (e.g., one or more of the reference numbers 102, 106, 108, 120, 202, and 204) are repeated in FIGS. 5-15 to illustrate similar elements. More particularly, the repeated reference numbers represent that each illustrated circuit has a fluid property measurement circuit 120 that is designed and configured based on the configuration of the sensor circuit within the same IC package. In addition, each of FIGS. 5-15 illustrates the fluid 102 in general (however this does not imply identical fluid types or concentrations).

Moreover, the embodiments illustrated in FIGS. 5-15 comprise a single IC chip included within or coupled to packaging material 202. In addition, the single IC chip shown in each of FIGS. 5-15 comprises a passivation layer 202, a top metal layer 204, material layers 106 (including one or more of polysilicon, dielectric, or metal layers) formed on a substrate 108, wherein the sensor circuit and the fluid property measurement circuit are formed in one or more of these layers. Also, direct physical connections are illustrated as the coupling means or mechanism between the sensor circuit and the fluid property measurement circuit shown in each of FIGS. 5-15. However, such physical connections can be replaced with wireless connections in any of these circuits, in alternative arrangements. Furthermore, other components within the IC circuit that may be used in a commercial embodiment such as power (e.g., AC voltage or current) supply sources, memory devices, microcontrollers, heaters, etc., are not shown for clarity of illustration.

Figure 5:
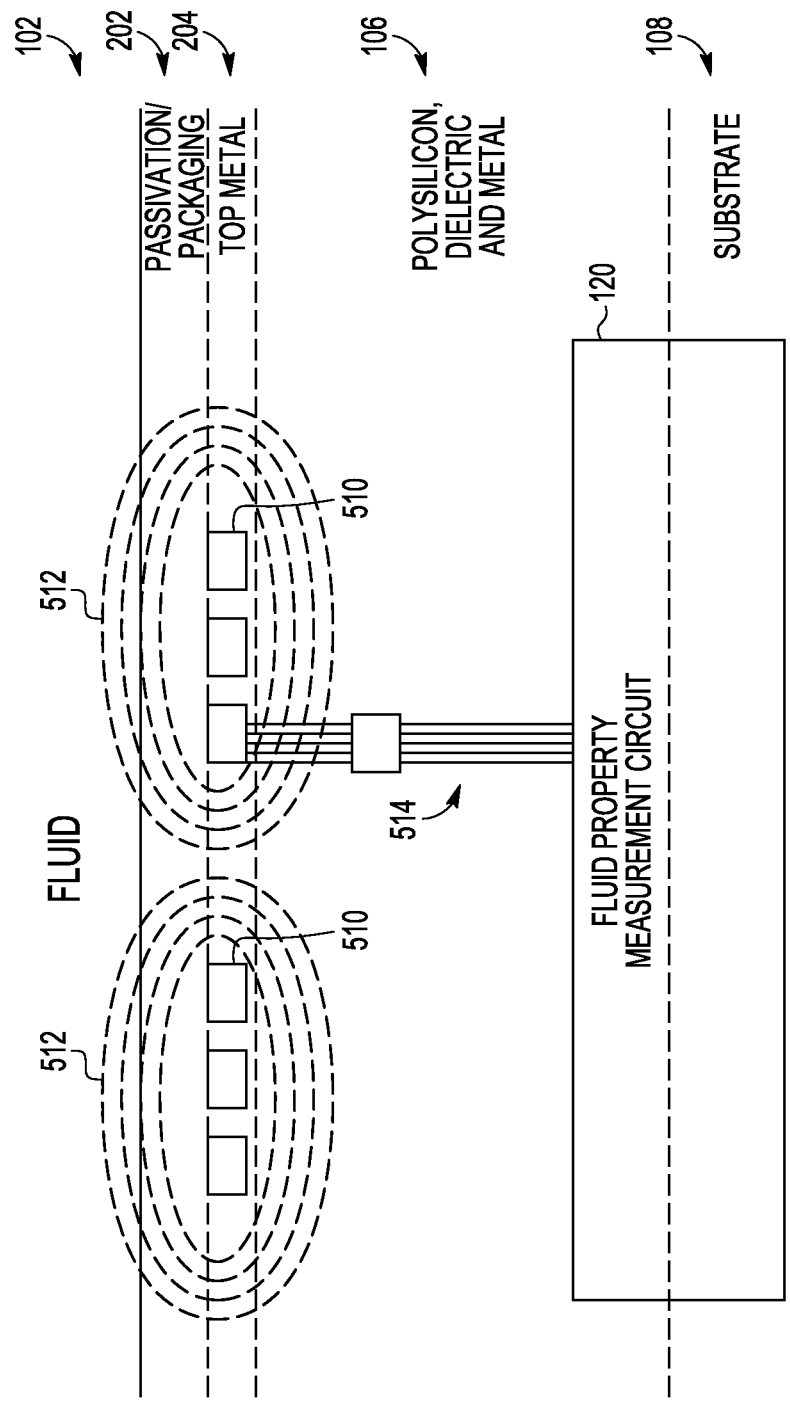
FIG. 5 is a conceptual cross-sectional view of an integrated circuit package for sensing one or more properties of a fluid, in accordance with another embodiment.

Turning first to FIG. 5, an IC package 500 is shown. The sensor circuit of the IC package comprises an inductor 510 that generates a magnetic field 512 that interacts with the fluid. In this embodiment, the inductor is formed in at least the top metal 204 of the IC with the passivation layer 202 covering the top metal layer. The inductor 510 is physically connected to the fluid property measurement circuit 120 using a set of one or more electrical connectors 514 formed in at least one metal layer 106.

Figure 6:
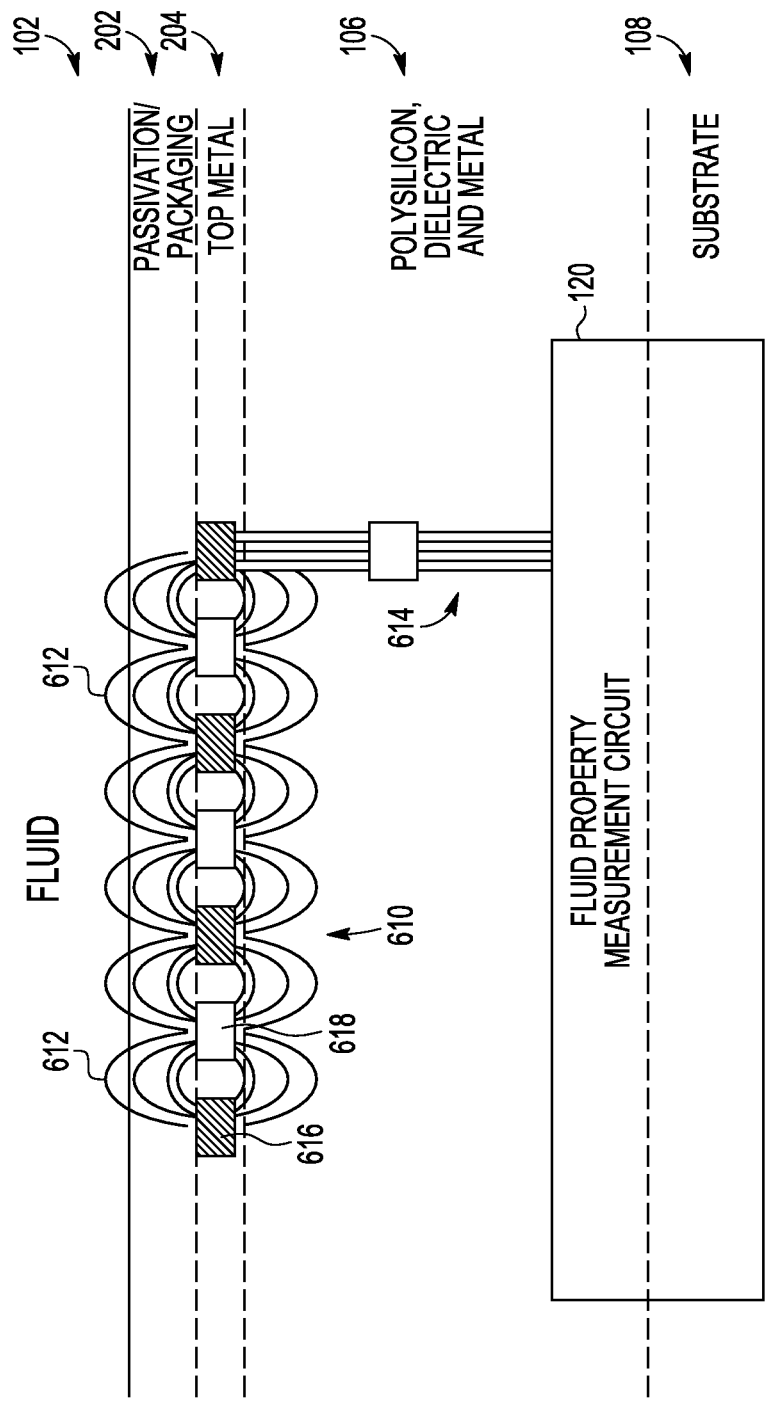
FIG. 6 is a conceptual cross-sectional view of an integrated circuit package for sensing one or more properties of a fluid, in accordance with another embodiment.

As shown in FIG. 6, an IC package 600 is shown. The sensor circuit of the IC package comprises an interdigitated comb capacitor 610 formed in at least the top metal layer 204 with the passivation layer 202 covering the top metal layer. These capacitors are, in general, usually formed on the same metal layers but can use different conductive layers. Although not shown in FIG. 6, both sides of the capacitor 610 are physically connected to the fluid property measurement circuit 120 using electrical connectors 614. In an embodiment, capacitor 610 is constructed of two printed circuit board tracks (i.e., the two capacitor plates) each having a "comb" shape comprising a plurality of fingers or teeth, respectively 616 and 618. The teeth 616 and 618 are, usually, within the same plane and face each other such that their fingers interleave without touching. The teeth 616 and 618 are connected outside of the plane at different voltages to create an electric field 612, some of which extends into or interacts with the fluid 102.

Figure 7:
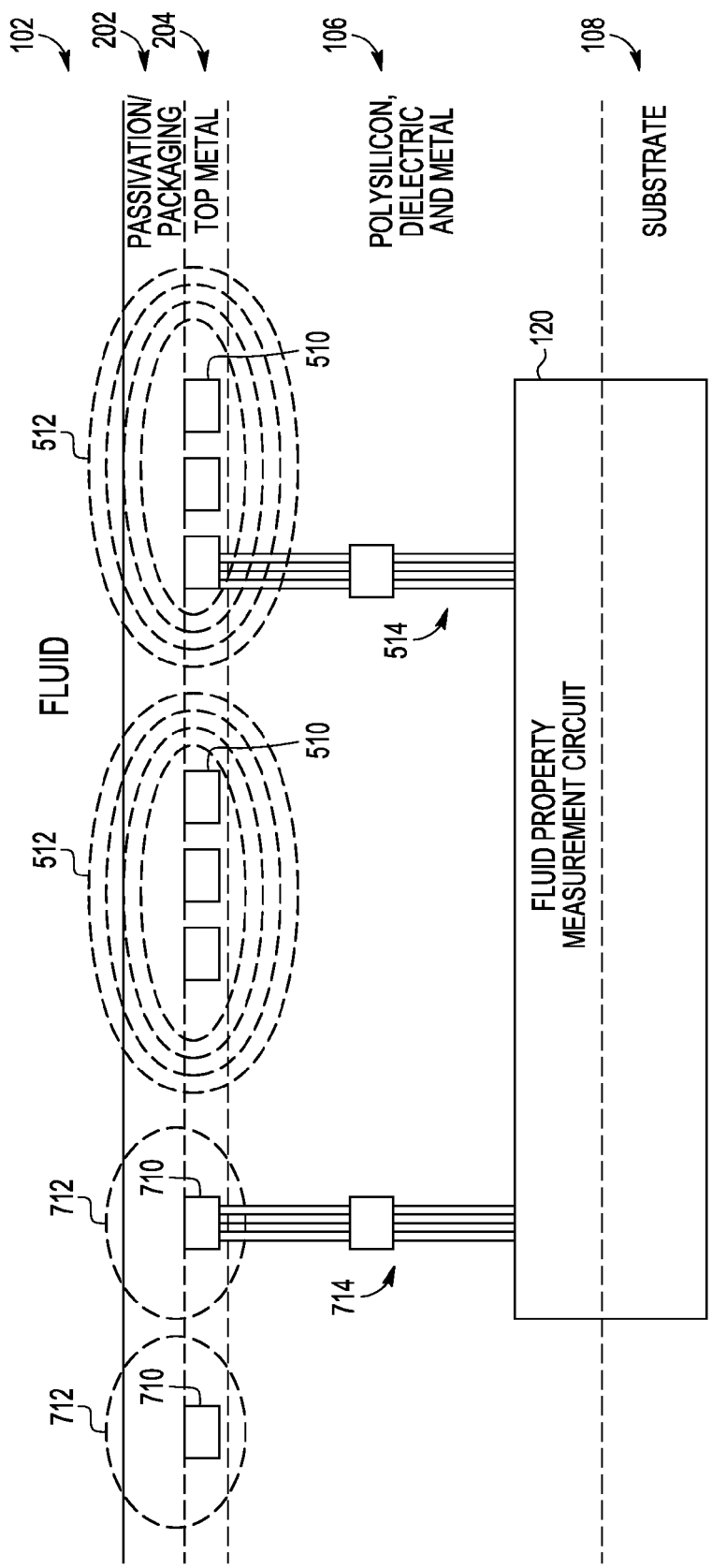
FIG. 7 is a conceptual cross-sectional view of an integrated circuit package for sensing one or more properties of a fluid, in accordance with another embodiment.

FIG. 7 shows an IC package 700 having a sensor circuit configuration comprising two inductors 510 (described by reference to FIG. 5) and 710 having different geometries, such as different numbers of turns, and/or different width of the coil, and/or different coil diameter and/or a different sized spacing between the turns. In this arrangement, both inductors are formed in the top metal layer 204 with the passivation layer 202 covering the top metal layer. Inductor 710 generates a magnetic field 712 that interacts with the fluid 102; and the inductor 710 is physically connected to the fluid property measurement circuit 120 using one or more electrical connectors 714 formed in at least one metal layer 106. This illustrative configuration could be used to determine the response of the ions within the fluid 102 at different frequencies and/or different penetration depths associated with the different inductors 510 and 710 for greater accuracy in detecting properties (e.g., fluid or ion type, ion concentration, etc.) of the fluid. Alternatively, each inductor is used to sense the properties of a different type of fluid.

In an alternative embodiment by reference to FIG. 7, IC package 700 is configured such that, for example, the field 712 generated by the inductor 710 does not interact with the fluid. However, there is a mutual inductance between the inductors 510 and 710. The fluid property measurement circuit is configured to determine the effect of the ions in the fluid on the self-inductance of the inductor 510 as well as on the mutual inductance between the two inductors 510 and 710 to, thereby, determine one or more properties of the fluid.

Figure 8:
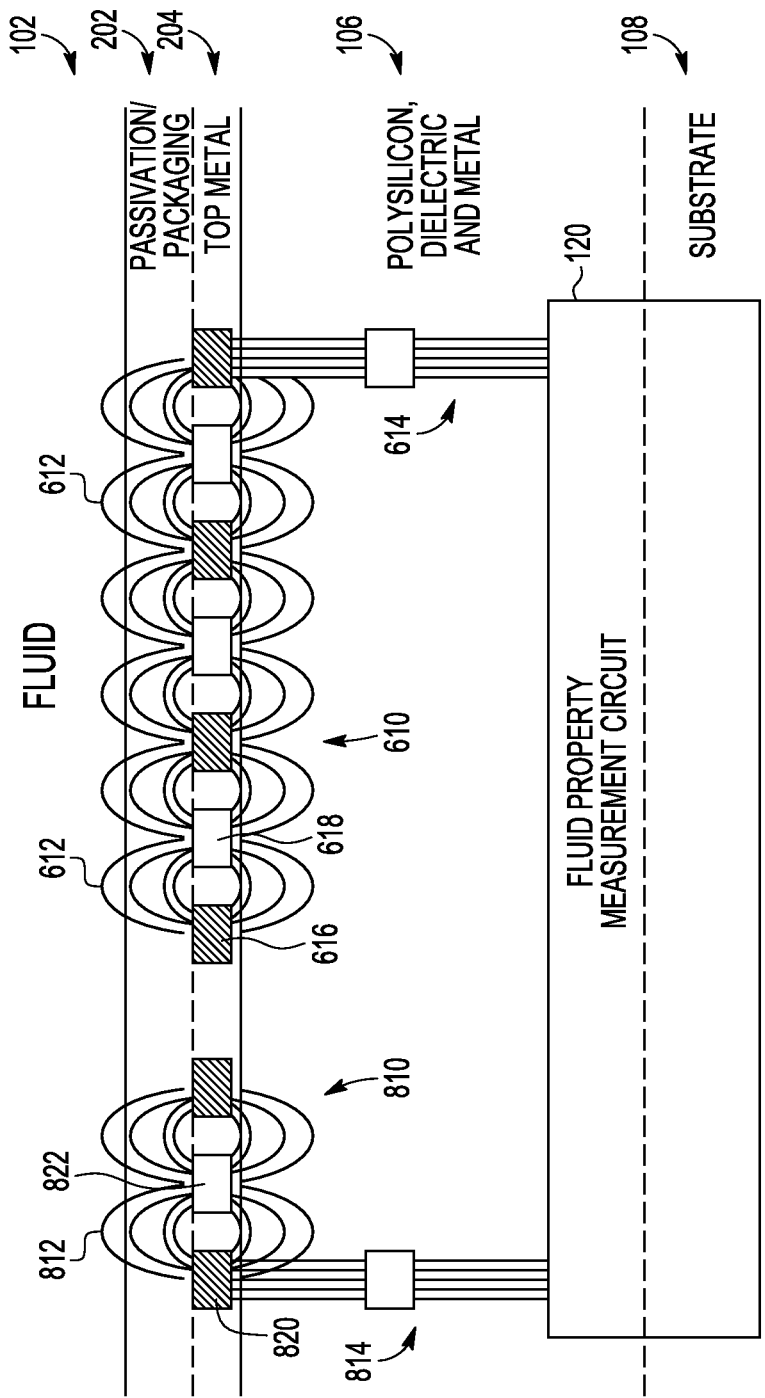
FIG. 8 is a conceptual cross-sectional view of an integrated circuit package for sensing one or more properties of a fluid, in accordance with another embodiment.

FIG. 8 shows an IC package 800 having a sensor circuit configuration comprising two interdigitated comb capacitors 610 (described by reference to FIG. 6) and 810 having different geometries, such as different numbers of fingers and/or geometries of fingers and/or a different sized spacing between the fingers. In this arrangement, both capacitors are formed in the top metal layer 204 with the passivation layer 202 covering the top metal layer. Capacitor 810 comprises interleaving fingers 820 and 822 charged to different voltages, which generates an electric field 812 that interacts with the fluid 102; and the capacitor 810 is physically connected to the fluid property measurement circuit 120 using one or more electrical connectors 814 formed in at least one metal layer 106. This illustrative configuration could be used to determine the response of the ions within the fluid 102 at different frequencies and/or different penetration depths associated with the different capacitors 610 and 810, for greater accuracy in detecting properties (e.g., fluid or ion type, ion concentration, etc.) of the fluid. Alternatively, each capacitor is used to sense the properties of a different type of fluid.

Figure 9:
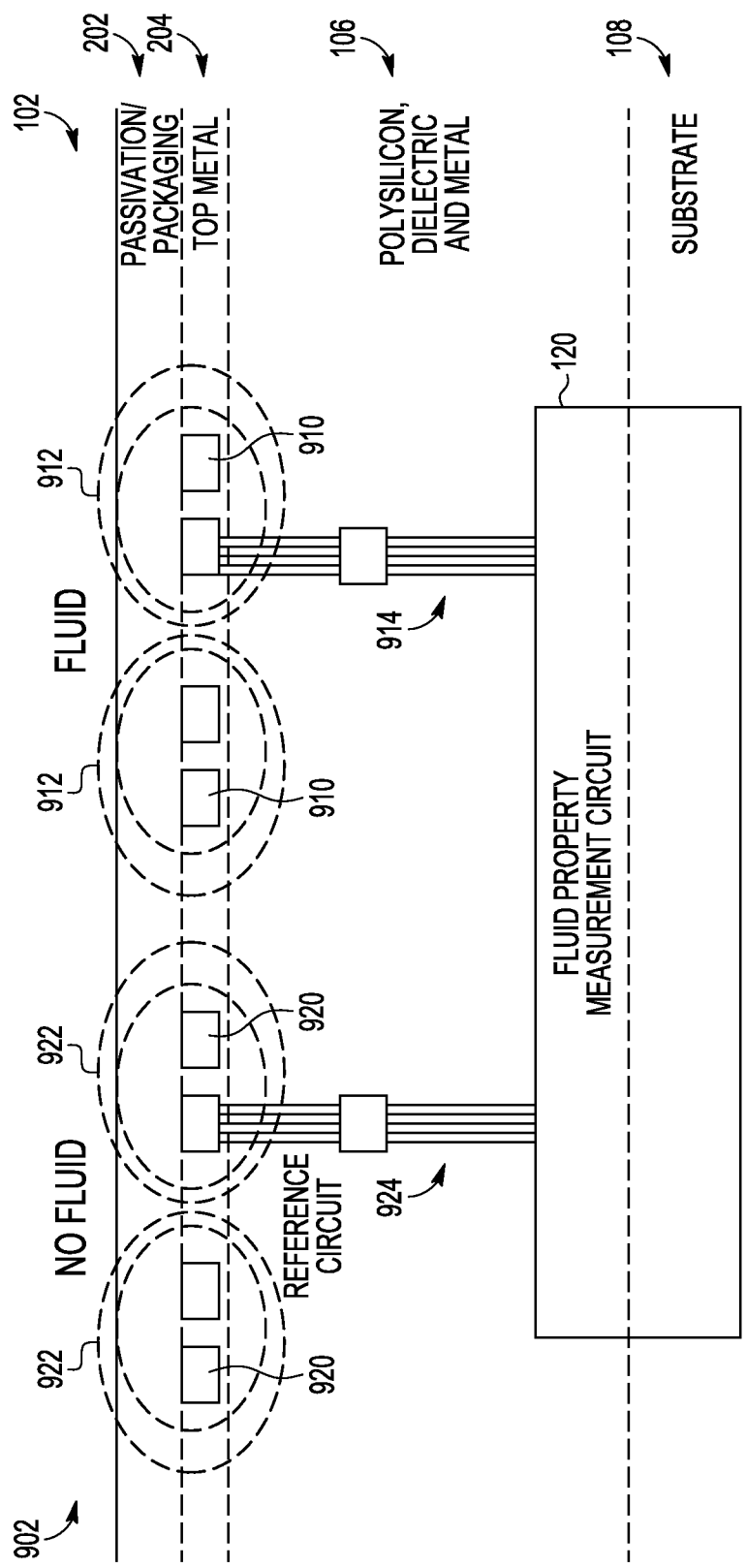
FIG. 9 is a conceptual cross-sectional view of an integrated circuit package for sensing one or more properties of a fluid, in accordance with another embodiment.

FIGS. 9-12 illustrate IC packages that contain reference circuits having properties against which the fluid property measurement circuit compares the measured properties of the sensor circuit to determine any relative changes. More particularly, FIG. 9 shows an IC package 900 that includes a sensor circuit comprising an inductor 910 and a reference circuit comprising an inductor 920 having matching (i.e., the same or substantially the same) geometries with the inductor 910 to create matching features, characteristics, and properties with the inductor 910. The inductor 910 generates a magnetic field 912 that interacts with the fluid 102. Whereas, the inductor 920 generates a magnetic field 922 that is not allowed to interact with the fluid (as shown by 902), such as by a manner in which the IC package is positioned relative to the fluid 102.

Figure 11:
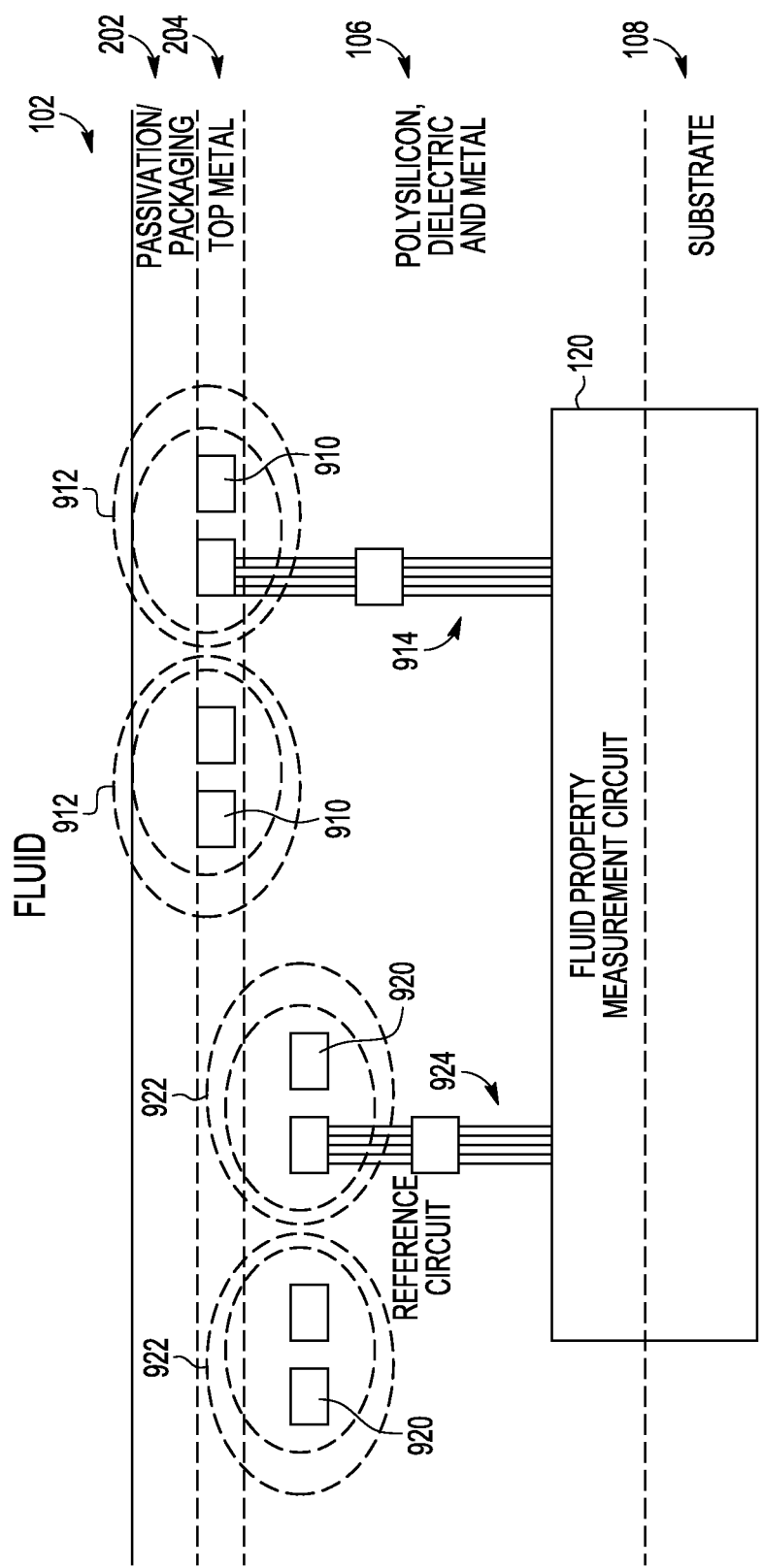
FIG. 11 is a conceptual cross-sectional view of an integrated circuit package for sensing one or more properties of a fluid, in accordance with another embodiment.

In this embodiment, both inductors 910 and 920 are formed in at least the top metal layer 204 of the IC chip 900 with the passivation layer 202 covering the top metal layer. The inductor 910 is physically connected to the fluid property measurement circuit 120 using a set of one or more electrical connectors 914 formed in at least one metal layer 106. The inductor 920 is physically connected to the fluid property measurement circuit 120 using a set of one or more electrical connectors 924 formed in at least one metal layer 106. FIG. 11 shows a similar IC package 1100 comprising the inductor 910 as the sensor circuit and the inductor 920 as the reference circuit. However, in this embodiment, the field 922 generated by the inductor 920 is prevented from interacting with the fluid by forming the reference circuit deeper within the IC chip in material layers 106.

Figure 10:
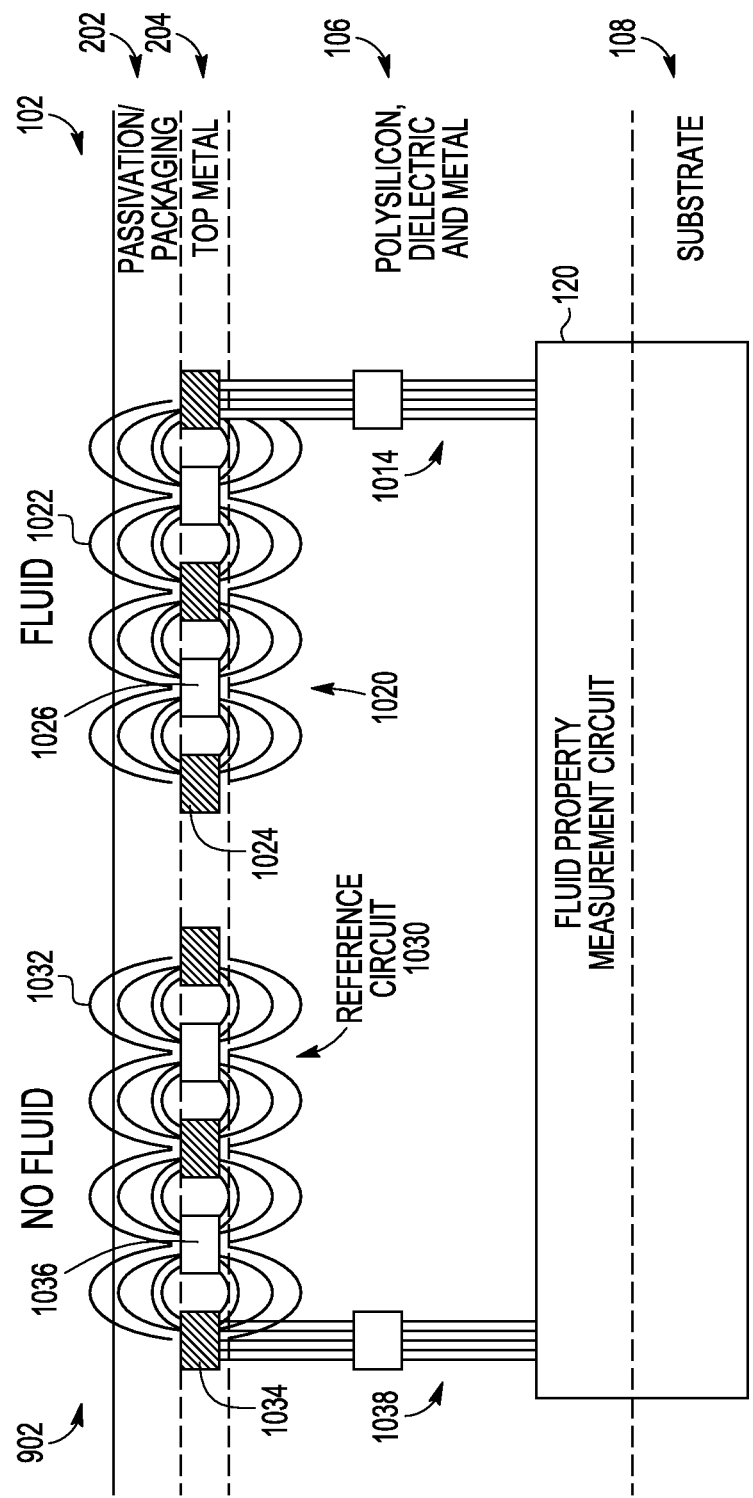
FIG. 10 is a conceptual cross-sectional view of an integrated circuit package for sensing one or more properties of a fluid, in accordance with another embodiment.

FIG. 10 shows an IC package 1000 that includes a sensor circuit comprising a capacitor 1020 and a reference circuit comprising a capacitor 1030 having matching (i.e., the same or substantially the same) geometries with the capacitor 1020 to create matching features, characteristics, and properties with the capacitor 1020. Capacitor 1020 comprises interleaving fingers 1024 and 1026 which, when charged to different voltages, generate an electric field 1022 that interacts with the fluid 102. Capacitor 1030 comprises interleaving fingers 1034 and 1036 which, when charged to different voltages, generate an electric field 1032 that is not allowed to interact with the fluid, such as by a manner in which the IC package is positioned relative to the fluid 102.

Figure 12:
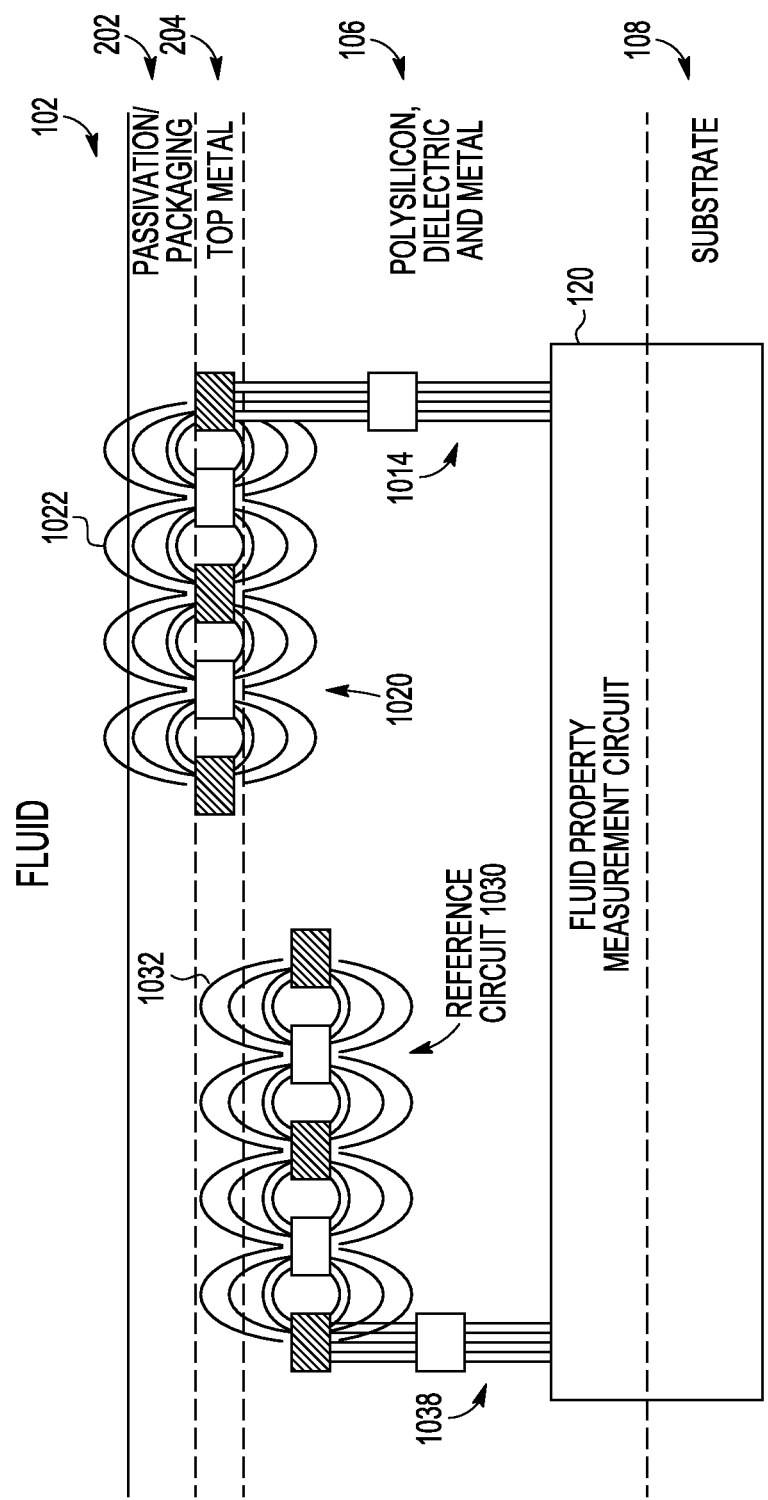
FIG. 12 is a conceptual cross-sectional view of an integrated circuit package for sensing one or more properties of a fluid, in accordance with another embodiment.

In this embodiment, both capacitors 1020 and 1030 are formed in at least the top metal layer 204 of the IC with the passivation layer 202 covering the top metal layer. The capacitor 1020 is physically connected to the fluid property measurement circuit 120 using a set of one or more electrical connectors 1014 formed in at least one metal layer 106. The capacitor 1030 is physically connected to the fluid property measurement circuit 120 using a set of one or more electrical connectors 1038 formed in at least one metal layer 106. FIG. 12 shows a similar IC package 1200 comprising the capacitor 1020 as the sensor circuit and the capacitor 1030 as the reference circuit. However, in this embodiment, the field 1032 generated by the capacitor 1030 is prevented from interacting with the fluid by forming the reference circuit deeper within the IC chip in material layers 106.

Figure 13:
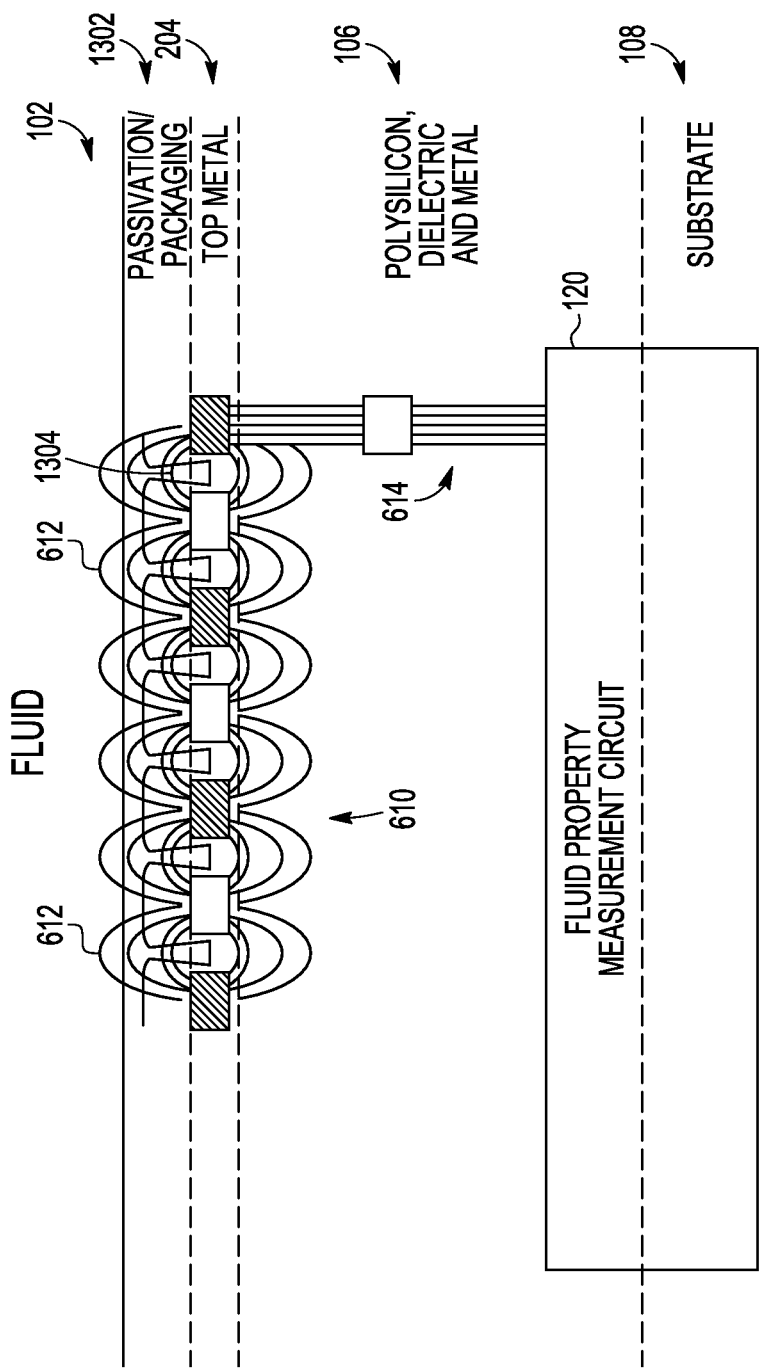
FIG. 13 is a conceptual cross-sectional view of an integrated circuit package for sensing one or more properties of a fluid, in accordance with another embodiment.
Figure 14:
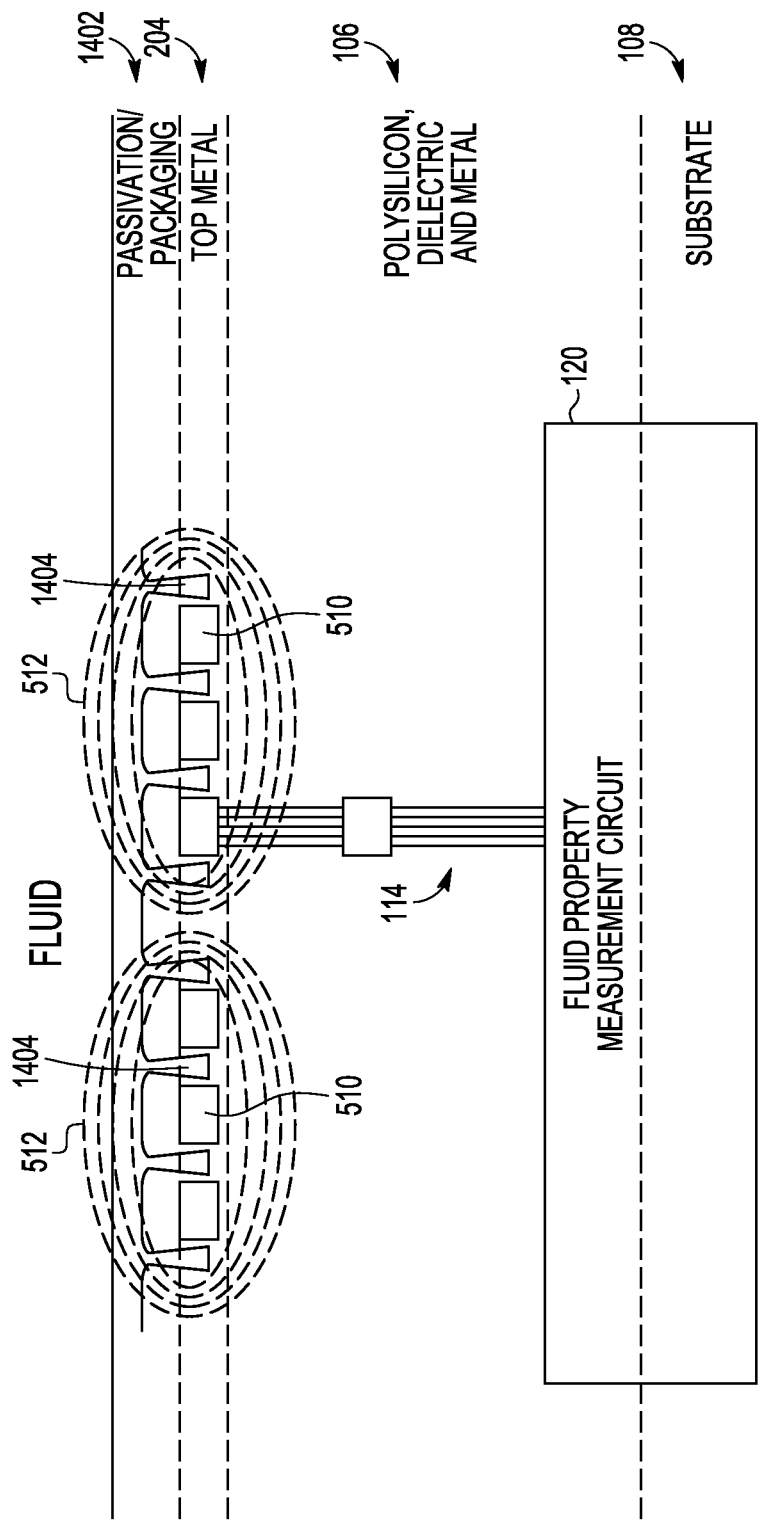
FIG. 14 is a conceptual cross-sectional view of an integrated circuit package for sensing one or more properties of a fluid, in accordance with another embodiment.

FIGS. 13 and 14 illustrate embodiments wherein the IC package comprises a (e.g., top) metal layer 204 formed on the substrate 108 and a passivation layer covering the metal layer 204, wherein the sensor circuit is formed in at least the metal layer 204, and wherein the passivation layer is fabricated with at least one groove to receive the fluid 102. The IC fabrication process normally creates a passivation layer that is substantially planar or flat. However, in accordance with these embodiments, the IC fabrication process is modified to deliberately create a non-planar passivation layer having grooves at certain locations. For example, etching is used during the IC manufacturing process to create openings or apertures in the passivation layer at desired locations to create the grooves. In an embodiment, an etching process is used that is similar to that used during standard CMOS manufacturing to etch away the passivation layer above a top metal layer to create contacts or pads for circuit components on an IC. These grooves act as a receptacle for the fluid 102 to enable the fluid to be closer to the field generated by the sensor circuit. The packaging material used in the IC package, in accordance with the embodiments shown in FIGS. 13 and 14 enables contact of the fluid with the IC chip. This configuration of passivation layer may be useful for sensing fluids that have a low ionic content.

More particularly, FIG. 13 shows an IC package 1300 that is similar to the IC package shown in FIG. 6, wherein the sensor circuit comprises the capacitor 610 formed in the top metal layer 204. However, the difference is that a passivation layer 1302 and any other insulating layer covering the capacitor comprises (in this case) a plurality of grooves or pockets 1304. In an embodiment, a groove 1304 is formed in the passivation layer 1302 between each two consecutive interwoven fingers. In other arrangements more or fewer grooves are used.

FIG. 14 shows an IC package 1400 that is similar to the IC package shown in FIG. 5, wherein the sensor circuit comprises the inductor 510 formed in the top metal layer 204. However, the difference is that a passivation layer 1402 and any other insulating layer covering the inductor comprises (in this case) a plurality of grooves or pockets 1404. In an embodiment, a groove 1404 is formed in the passivation layer 1402 between each two consecutive turns of the inductor 510. In other arrangements more or fewer grooves are used.

Figure 15:
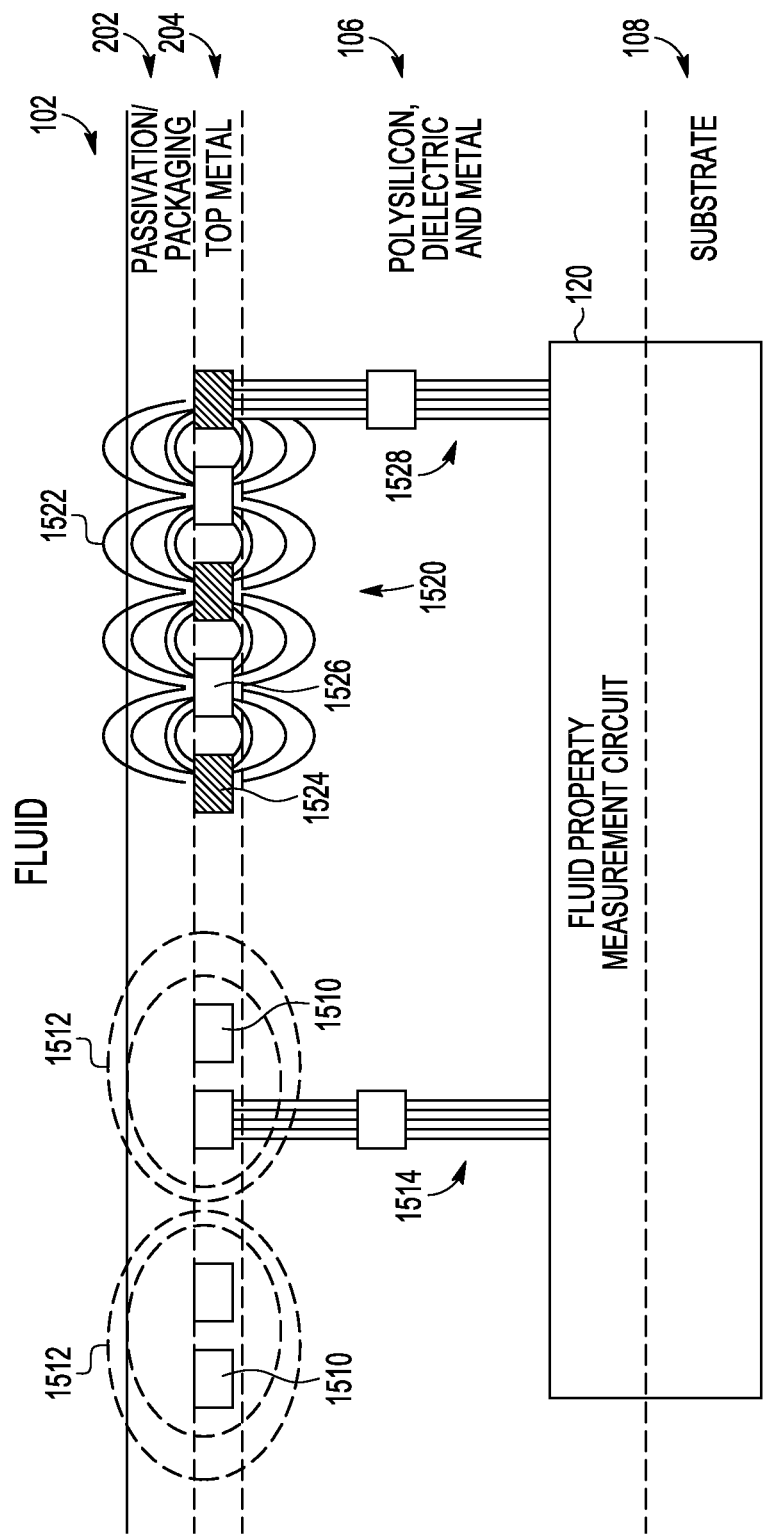
FIG. 15 is a conceptual cross-sectional view of an integrated circuit package for sensing one or more properties of a fluid, in accordance with another embodiment.

FIG. 15 shows an IC package 1500 having a sensor circuit that comprises an LC circuit. The LC circuit includes a capacitor 1520 and an inductor 1510 formed in a top metal layer 204 with a passivation layer 202 covering the top metal layer 204. The inductor 1510 generates a magnetic field 1512 that may interact with the fluid 102; and the capacitor 1520 comprises interleaving fingers 1524 and 1526 which, when charged to different voltages, generate an electric field 1522 that may interact with the fluid 102, so that either field or both interact with the fluid. The capacitor 1520 is physically connected to the fluid property measurement circuit 120 using a set of one or more electrical connectors 1528 formed in at least one metal layer 106. The inductor 1510 is physically connected to the fluid property measurement circuit 120 using a set of one or more electrical connectors 1514 formed in at least one metal layer 106. This LC circuit is characterized by a resonant frequency that depends at least in part on the geometries of the components and the properties of the fluid 102.

Figure 18:
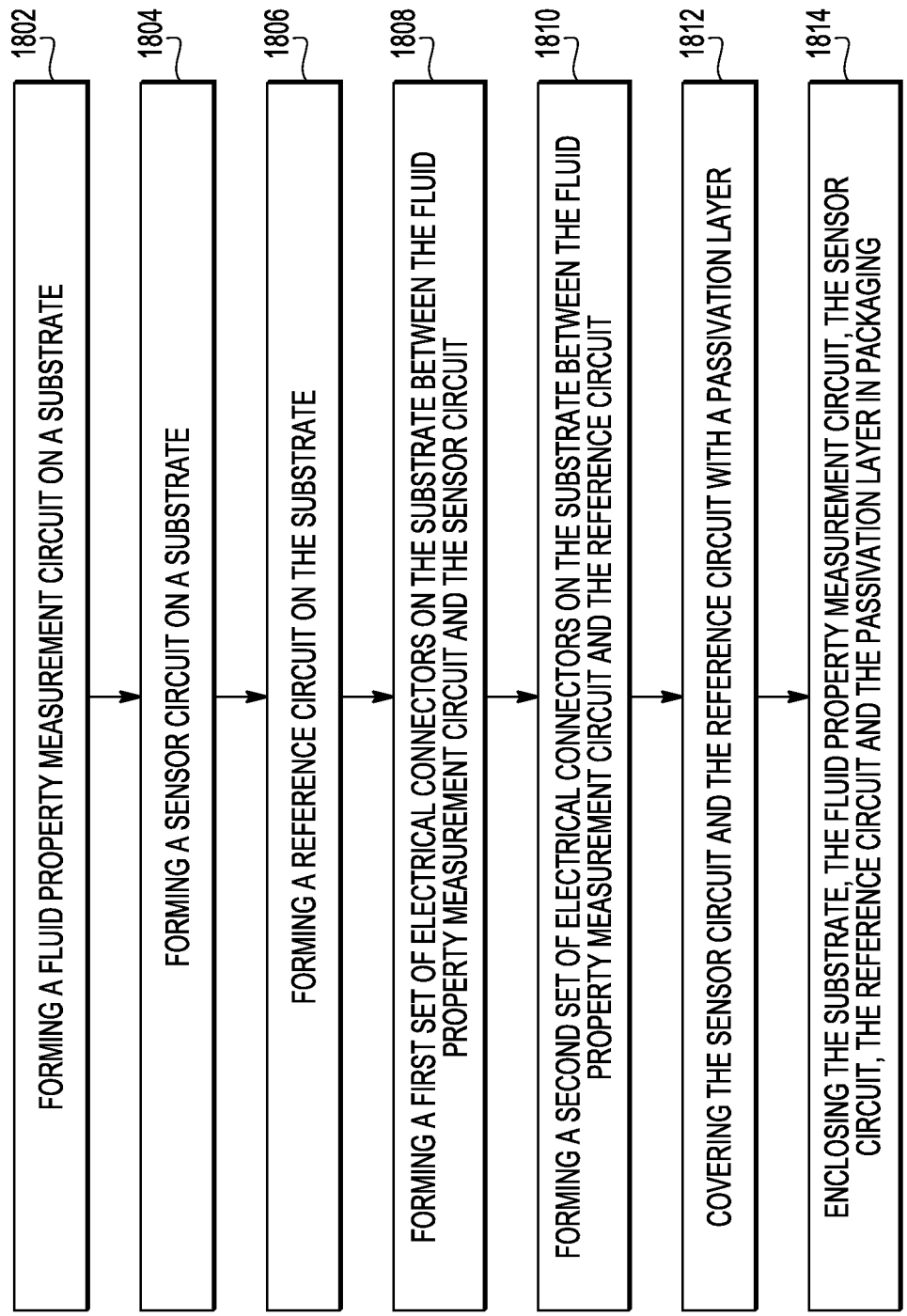
FIG. 18 is a flow diagram illustrating a method of fabricating an integrated circuit package for sensing one or more properties of a fluid, in accordance with an embodiment.

Turning now to FIG. 18, illustrated therein is a flow diagram illustrating a general method 1800 of fabricating an integrated circuit package for sensing one or more properties of a fluid, in accordance with an embodiment. This illustrative IC fabrication process 1800 can be used to fabricate any of the circuits shown in FIGS. 1-3 and 5-15. IC fabrication process 1800 comprises forming a fluid property measurement circuit on a substrate, at 1802. At 1804, process 1800 further comprises forming a sensor circuit that is configured to generate a field that interacts with a fluid, wherein the sensor circuit and the fluid property measurement circuit are formed within a same integrated circuit package. The fluid property measurement circuit is configured to determine a change in a property of the sensor circuit as results from the field contacting the fluid and is further configured to determine a property of the fluid based on the change in the property of the sensor circuit.

In one particular embodiment, the sensor circuit is formed on the same substrate (i.e., the same IC chip) with the fluid property measurement circuit, and the process 1800 comprises covering (1812) the sensor circuit with a passivation layer. In alternative embodiment, the sensor circuit is formed on a separate IC chip. In a further embodiment, the IC fabrication process 1800 comprises forming (1806) a reference circuit on the same substrate such that the passivation layer also covers (1812) the reference circuit and such that the reference circuit has at least one matching property with the sensor circuit. Both the sensor circuit and the reference circuit are fabricated to be coupled (e.g., physically or wirelessly for instance) to the fluid property measurement circuit on the substrate.

In an example implementation where the coupling is a physical coupling, the IC fabrication process comprises forming (1808) a first set of electrical connectors on the substrate between the fluid property measurement circuit and the sensor circuit and forming (1810) a second set of electrical connectors on the substrate between the fluid property measurement circuit and the reference circuit. In an embodiment, the fluid property measurement circuit is formed on the substrate. Afterward, the electrical connectors are formed before the sensor circuit and reference circuit are formed on the substrate. Upon being implemented to fabricate the IC chip(s) containing its interconnected components and circuits, the IC fabrication process 1800 (in one embodiment) comprises enclosing (1814) the substrate, the fluid property measurement circuit, the sensor circuit, the reference circuit and the passivation layer in packaging material that is impenetrable by the fluid. However, different embodiments may require the packaging step configure the packaging for the IC chip(s) to allow access by the fluid into or over the packaging material.

Benefits of the present disclosure include, but are not limited to the following. The use of electromagnetic fields to probe the fluid enables the use of packaging material that seals the Si ICs from the possibly corrosive fluid. This prolongs the operational life of the IC, which is important in continuous monitoring applications. Integration of the sensor and fluid property measurement circuits in the same integrated circuit package enables better measurement sensitivity than the remote options in the prior art. Embodiments of the present teaching can be implemented using conventional CMOS technology. This allows the cost to be minimized and the scope of applications that utilize such embodiments to be maximized. The integration of all the components in conventional CMOS enables and simplifies further integration of digital processing power and non-volatile storage of relevant algorithms and parameters so that complete end-to-end measurement, processing and actuation can be executed by a single integrated circuit package. Moreover, non-expert users can utilize these packages since the available expert knowledge is now captured in the stored algorithms and database.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

For the sake of brevity, conventional techniques related to semiconductor fabrication (including those using conventional CMOS technology), CMOS devices, MOSFETs, ion-sensitive devices, inductors (L), capacitors (C), and LC circuits (also referred to herein as LC tanks), frequency sensing circuits, and other functional aspects of the systems (and the individual operating components of the systems) may not be described in detail. Furthermore, the connecting lines shown in the various figures contained herein are intended to represent example physical and/or electrical couplings between the various elements. It should be noted that many alternative or additional physical or electrical connections, such as wireless connections, may be present in a practical embodiment. Moreover, the various IC embodiments described above (e.g., with respect to FIGS. 1-3 and 5-14) may be produced or fabricated using conventional semiconductor processing techniques, e.g., well-known CMOS techniques. Further a variety of well-known and common semiconductor materials may be used, e.g., traditional metals (aluminum, copper, gold, etc.), polysilicon, silicon dioxide, silicon nitride, silicon, and the like.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

In this document, the terms "comprises," "comprising," "has", "having," "includes", "including," "contains", "containing", "made of" or any other variation thereof, are intended to cover a non-exclusive inclusion, such that a process, method, article, or apparatus that comprises, has, includes, contains, is made of a list of elements does not include only those elements but may include other elements not expressly listed or inherent to such process, method, article, or apparatus. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%.

As used herein, the terms "configured to", "configured with", "arranged to", "arranged with", "capable of" and any like or similar terms mean that the referenced circuit elements have an internal physical arrangement (such as by virtue of a particular transistor or fabrication technology used) and/or physical coupling and/or connectivity with other circuit elements in an inactive state. This physical arrangement and/or physical coupling and/or connectivity (while in the inactive state) enable the circuit elements to perform stated functionality while in the active state of receiving and processing various signals or inputs to the circuit elements. A device or structure that is "configured" in a certain way is configured in at least that way, but may also be configured in ways that are not listed.

The above description refers to elements, nodes or features being "connected" or "coupled" together. As used here and, unless expressly stated otherwise, "coupled" means that one element, node or feature is directly or indirectly joined to (or is in direct or indirect communication with) another element, node or feature, and not necessarily physically. As used herein, unless expressly stated otherwise, "connected" means that one element, node or feature is directly joined to (or is in direct communication with) another element, node or feature. Furthermore, although the various circuit schematics shown herein depict certain example arrangement of elements, additional intervening elements, devices, features, or components may be present in an actual embodiment (assuming that the functionality of the given circuit is not adversely affected).

In the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An integrated circuit package for sensing fluid properties, comprising:
   a substrate comprising semiconductor material;
   a fluid property measurement circuit formed on the substrate;
   a sensor circuit coupled to the fluid property measurement circuit within a same integrated circuit package;
   wherein the sensor circuit is configured to generate a field that interacts with the fluid;
   wherein the fluid property measurement circuit is configured to determine a change in a property of the sensor circuit as results from the field interacting with the fluid and is further configured to determine a property of the fluid based on the change in the property of the sensor circuit.

2. The integrated circuit package of claim 1 further comprising packaging material configured to prevent direct physical contact of the fluid with the substrate, the fluid property measurement circuit, and the sensor circuit.

3. The integrated circuit package of claim 1, wherein the sensor circuit comprises at least one inductor component.

4. The integrated circuit package of claim 3, wherein the at least one inductor component comprises a first inductor component having a first geometry and a second inductor component having a second geometry that is different than the first geometry of the first inductor component.

5. The integrated circuit package of claim 1, wherein the sensor circuit comprises at least one capacitor component.

6. The integrated circuit package of claim 5, wherein the at least one capacitor component comprises a first capacitor component having a first geometry and a second capacitor component having a second geometry that is different than the first geometry of the first capacitor component.

7. The integrated circuit package of claim 5, wherein the at least one capacitor component comprises at least one interdigitated comb capacitor.

8. The integrated circuit package of claim 1, wherein the sensor circuit comprises at least one inductor component and at least one capacitor component.

9. The integrated circuit package of claim 1, wherein the sensor circuit and the fluid property measurement circuit are formed on a same integrated circuit chip.

10. The integrated circuit package of claim 9, wherein the sensor circuit is formed in at least a top metal layer of the integrated circuit chip.

11. The integrated circuit of claim 10, wherein the integrated circuit chip further comprises a passivation layer covering the top metal layer.

12. The integrated circuit of claim 11, wherein the passivation layer comprises at least one of silicon oxide, silicon nitride, or silicon oxi-nitride.

13. The integrated circuit package of claim 1 further comprising a reference circuit formed on the substrate and coupled to the fluid property measurement circuit, wherein the reference circuit is configured to generate a field that matches the field generated by the sensor circuit in a known calibration state.

14. The integrated circuit package of claim 1 further comprising a passivation layer and a metal layer between the sensor circuit and the fluid property measurement circuit, wherein the sensor circuit is formed on the passivation layer.

15. The integrated circuit package of claim 1 further comprising a metal layer formed on the substrate and a passivation layer covering the metal layer, wherein the sensor circuit is formed in at least the metal layer, and wherein the passivation layer is fabricated with at least one groove to receive the liquid.

16. A method of fabricating an integrated circuit package for sensing fluid properties, the method comprising:
   forming a fluid property measurement circuit on a substrate;
   forming a sensor circuit that is configured to generate a field that interacts with a fluid and covering the sensor circuit with a passivation layer, wherein the sensor circuit and the fluid property measurement circuit are electrically coupled together and formed within a same integrated circuit package, wherein the fluid property measurement circuit is configured to determine a change in a property of the sensor circuit as results from the field interacting with the fluid and is further configured to determine a property of the fluid based on the change in the property of the sensor circuit;
   enclosing the substrate, the fluid property measurement circuit, the sensor circuit, the reference circuit and the passivation layer in packaging material that is impenetrable by the fluid.

17. A method performed by an integrated circuit package for determining fluid properties, the method comprising:
   sensing a property of a fluid using a first field that is generated by a sensor circuit and that interacts with the fluid;
   determining, by a fluid property measurement circuit formed on a substrate and coupled to the sensor circuit within a same integrated circuit package, a change in a property of the sensor circuit associated with the first field interacting with the fluid;
   determining, by the fluid property measurement circuit, the sensed property of the fluid using the determined change in the property of the sensor circuit.

18. The method of claim 17, wherein determining the change in the property of the sensor circuit comprises determining a change in resonant frequency of the sensor circuit.

19. The method of claim 18, wherein determining the change in resonant frequency of the sensor circuit comprises comparing a first resonant frequency measured for the sensor circuit while the first field interacts with the fluid to a second resonant frequency of a reference circuit within the same integrated circuit package and positioned to prevent a second field generated by the reference circuit from interacting with the fluid.

20. The method of claim 17, wherein the sensing is performed without the fluid physically contacting the substrate, the fluid property measurement circuit, or the sensor circuit.

* * * * *